US007232924B2

(12) United States Patent
Raillard et al.

(10) Patent No.: US 7,232,924 B2
(45) Date of Patent: Jun. 19, 2007

(54) METHODS FOR SYNTHESIS OF ACYLOXYALKYL DERIVATIVES OF GABA ANALOGS

(75) Inventors: Stephen P. Raillard, Mountain View, CA (US); Cindy X. Zhou, Palo Alto, CA (US); Fenmei Yao, Mountain View, CA (US); Suresh Kumar Manthati, Cupertino, CA (US); Jia-Ning Xiang, Palo Alto, CA (US); Mark A. Gallop, Los Altos, CA (US)

(73) Assignee: Xenoport, Inc., Santa Clara, CA (US)

( * ) Notice: Subject to any disclaimer, the term of this patent is extended or adjusted under 35 U.S.C. 154(b) by 530 days.

(21) Appl. No.: 10/460,091

(22) Filed: Jun. 11, 2003

(65) Prior Publication Data
US 2004/0014940 A1 Jan. 22, 2004

Related U.S. Application Data

(63) Continuation-in-part of application No. 10/171,485, filed on Jun. 11, 2002, now Pat. No. 6,818,787.

(60) Provisional application No. 60/366,090, filed on Mar. 19, 2002, provisional application No. 60/298,514, filed on Jun. 14, 2001, provisional application No. 60/297,521, filed on Jun. 11, 2001.

(51) Int. Cl.
C07C 271/22 (2006.01)
(52) U.S. Cl. ..................................................... 560/115
(58) Field of Classification Search .................. 560/115
See application file for complete search history.

(56) References Cited

U.S. PATENT DOCUMENTS

| 2,996,431 A | 8/1961 | Barry |
| 3,139,383 A | 6/1964 | Neville, Jr. |
| 3,402,240 A | 9/1968 | Cain et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien |
| 4,024,175 A | 5/1977 | Satzinger et al. |
| 4,036,829 A | 7/1977 | Ferres et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi |
| 4,083,949 A | 4/1978 | Benedikt |
| 4,087,544 A | 5/1978 | Satzinger et al. |
| 4,088,864 A | 5/1978 | Theeuwes et al. |
| 4,093,709 A | 6/1978 | Choi et al. |
| 4,189,571 A | 2/1980 | Bodor et al. |
| 4,200,098 A | 4/1980 | Ayer et al. |
| 4,285,987 A | 8/1981 | Ayer et al. |
| 4,377,590 A | 3/1983 | Myers et al. |
| 4,421,736 A | 12/1983 | Walters |
| 4,434,153 A | 2/1984 | Urquhart et al. |
| 4,611,056 A | 9/1986 | Guindon et al. |
| 4,721,613 A | 1/1988 | Urquhart et al. |
| 4,752,470 A | 6/1988 | Mehta |
| 4,760,057 A | 7/1988 | Alexander |
| 4,816,263 A | 3/1989 | Ayer et al. |
| 4,820,523 A | 4/1989 | Shtohryn et al. |
| 4,853,229 A | 8/1989 | Theeuwes |
| 4,916,230 A | 4/1990 | Alexander |
| 4,996,058 A | 2/1991 | Sinnreich et al. |
| 5,051,448 A | 9/1991 | Shashoua |
| 5,084,479 A | 1/1992 | Woodruff |
| 5,091,184 A | 2/1992 | Khanna |
| 5,112,598 A | 5/1992 | Biesalski |
| 5,281,585 A | 1/1994 | Duggan et al. |
| 5,401,868 A | 3/1995 | Lund |
| 5,466,811 A | 11/1995 | Alexander |
| 5,556,611 A | 9/1996 | Biesalski |
| 5,563,175 A | 10/1996 | Silverman et al. |
| 5,580,872 A | 12/1996 | Chu et al. |
| 5,599,973 A | 2/1997 | Silverman et al. |
| 5,602,118 A | 2/1997 | Lin et al. |
| 5,622,944 A | 4/1997 | Hale et al. |
| 5,672,584 A | 9/1997 | Borchardt et al. |
| 5,684,018 A | 11/1997 | Alexander |
| 5,698,155 A | 12/1997 | Grosswald et al. |
| 6,001,876 A | 12/1999 | Singh |
| 6,020,370 A | 2/2000 | Horwell et al. |

(Continued)

FOREIGN PATENT DOCUMENTS

| CA | 1085420 A1 | 9/1980 |
| DE | 4424975 A1 | 1/1996 |
| DE | 19804085 A1 | 8/1999 |
| DE | 19816983 A1 | 10/1999 |
| EP | 23192 B1 | 3/1984 |

(Continued)

OTHER PUBLICATIONS

U.S. Appl. No. 10/171,485, Gallop et al.
U.S. Appl. No. 10/167,797, Gallop et al.
U.S. Appl. No. 10/170,127, Gallop et al.
U.S. Appl. No. 10/313,825, Gallop et al.
Albrecht et al., "Modular Branched Peptides: Synthesis of Potential Branched Peptide Vaccines," *Pept. Chem. Struct. Biol. Proc. Am. Pept. Sym.*, 11th (1990), Meeting Date3 (1989) 718-720.

(Continued)

*Primary Examiner*—James O. Wilson
*Assistant Examiner*—Paul V. Ward
(74) *Attorney, Agent, or Firm*—Dorsey & Whitney LLP

(57) ABSTRACT

The synthesis of 1-(acyloxy)-alkyl carbamates of GABA analogs from 1-haloalkyl carbamates of GABA analogs are described. Also described are new 1-haloalkyl carbamates of GABA analogs.

27 Claims, No Drawings

U.S. PATENT DOCUMENTS

| | | |
|---|---|---|
| 6,022,969 A | 2/2000 | Rice et al. |
| 6,024,977 A | 2/2000 | Yatvin et al. |
| 6,028,214 A | 2/2000 | Silverman et al. |
| 6,054,482 A | 4/2000 | Augurt et al. |
| 6,103,932 A | 8/2000 | Horwell et al. |
| 6,117,906 A | 9/2000 | Silverman et al. |
| 6,127,418 A | 10/2000 | Bueno et al. |
| 6,171,615 B1 | 1/2001 | Roussin et al. |
| 6,375,987 B1 | 4/2002 | Farah et al. |
| 6,379,700 B2 | 4/2002 | Joachim et al. |
| 2002/0028806 A1 | 3/2002 | Goebel et al. |
| 2002/0055522 A1 | 5/2002 | Liebeschuetz et al. |
| 2002/0107208 A1 | 8/2002 | Chen et al. |
| 2003/0083382 A1 | 5/2003 | Cundy et al. |
| 2003/0104053 A1 | 6/2003 | Gusler et al. |

FOREIGN PATENT DOCUMENTS

| | | |
|---|---|---|
| EP | 0136893 A2 | 4/1985 |
| EP | 0138481 B1 | 4/1985 |
| EP | 200692 B1 | 11/1986 |
| EP | 69378 B1 | 1/1987 |
| EP | 70204 A2 | 11/1987 |
| EP | 335545 B2 | 10/1989 |
| EP | 429232 A1 | 5/1991 |
| EP | 458751 A1 | 11/1991 |
| EP | 234485 B1 | 4/1992 |
| EP | 416373 A3 | 5/1992 |
| EP | 587134 A3 | 7/1994 |
| EP | 381661 A1 | 5/1995 |
| EP | 381661 B1 | 5/1995 |
| EP | 584694 B1 | 1/1998 |
| EP | 617036 A3 | 1/1998 |
| EP | 327766 B1 | 4/1998 |
| EP | 567966 B1 | 9/1998 |
| EP | 781778 B1 | 4/2000 |
| EP | 656348 A3 | 5/2000 |
| EP | 656348 B1 | 5/2000 |
| EP | 1178034 A1 | 2/2002 |
| EP | 1201240 A2 | 5/2002 |
| EP | 1226820 A1 | 7/2002 |
| FR | 2476087 B1 | 7/1983 |
| FR | 2570695 A1 | 3/1986 |
| FR | 2783521 B1 | 4/2002 |
| GB | 2362646 A1 | 11/2001 |
| JP | 54055562 A2 | 5/1979 |
| JP | 55015432 B4 | 2/1980 |
| JP | 57021400 A2 | 2/1982 |
| JP | 58222089 A2 | 12/1983 |
| JP | 59219268 A2 | 12/1984 |
| JP | 01113391 A2 | 5/1989 |
| JP | 01275565 A2 | 11/1989 |
| JP | 03072476 A2 | 3/1991 |
| JP | 05202059 A2 | 8/1993 |
| JP | 06228103 A2 | 8/1994 |
| JP | 06228149 A2 | 8/1994 |
| JP | 08217787 A2 | 8/1996 |
| JP | 08295668 A2 | 11/1996 |
| JP | 09015799 A2 | 1/1997 |
| JP | 09080709 A2 | 3/1997 |
| JP | 10287669 A2 | 10/1998 |
| JP | 11029533 A2 | 2/1999 |
| JP | 11199573 A2 | 7/1999 |
| JP | 200344774 A2 | 12/2000 |
| JP | 03190857 B2 | 7/2001 |
| JP | 2002105041 A2 | 4/2002 |
| WO | WO 90/11300 A1 | 10/1990 |
| WO | WO 91/10639 A1 | 7/1991 |
| WO | WO 92/09560 A1 | 6/1992 |
| WO | WO 93/18070 A1 | 9/1993 |
| WO | WO 93/23383 A1 | 11/1993 |
| WO | WO 93/25197 A1 | 12/1993 |
| WO | WO 94/20508 A1 | 9/1994 |
| WO | WO 95/10519 A1 | 4/1995 |
| WO | WO 95/25106 A1 | 9/1995 |
| WO | WO 95/33720 A1 | 12/1995 |
| WO | WO 96/09297 A1 | 3/1996 |
| WO | WO 09613497 A1 | 5/1996 |
| WO | WO 96/20172 A1 | 7/1996 |
| WO | WO 96/36613 A1 | 11/1996 |
| WO | WO 96/38435 A1 | 12/1996 |
| WO | WO 96/39407 A1 | 12/1996 |
| WO | WO 97/23499 A1 | 7/1997 |
| WO | WO 97/29101 A1 | 8/1997 |
| WO | WO 97/33858 A1 | 9/1997 |
| WO | WO 97/33859 A1 | 9/1997 |
| WO | WO 98/04537 A1 | 2/1998 |
| WO | WO 98/06402 A1 | 2/1998 |
| WO | WO 98/09957 A1 | 3/1998 |
| WO | WO 98/15560 A1 | 4/1998 |
| WO | WO 98/17627 A1 | 4/1998 |
| WO | WO 98/25920 A1 | 6/1998 |
| WO | WO 98/39324 A1 | 9/1998 |
| WO | WO 98/54164 A1 | 12/1998 |
| WO | WO 99/00127 A1 | 1/1999 |
| WO | WO 99/06402 A1 | 2/1999 |
| WO | WO 99/08671 A1 | 2/1999 |
| WO | WO 99/11658 A1 | 3/1999 |
| WO | WO 99/21824 A1 | 5/1999 |
| WO | WO 99/31057 A1 | 6/1999 |
| WO | WO 99/31074 A2 | 6/1999 |
| WO | WO 99/31075 A1 | 6/1999 |
| WO | WO 99/32480 A1 | 7/1999 |
| WO | WO 99/37296 A1 | 7/1999 |
| WO | WO 99/38829 A1 | 8/1999 |
| WO | WO 99/40072 A1 | 8/1999 |
| WO | WO 99/40075 A1 | 8/1999 |
| WO | WO 99/52894 A1 | 10/1999 |
| WO | WO 99/52903 A1 | 10/1999 |
| WO | WO 99/57121 A1 | 11/1999 |
| WO | WO 99/61424 A1 | 12/1999 |
| WO | WO 00/15611 A1 | 3/2000 |
| WO | WO 00/01704 A3 | 4/2000 |
| WO | WO 00/23067 A1 | 4/2000 |
| WO | WO 00/31020 A1 | 6/2000 |
| WO | WO 00/31062 A1 | 6/2000 |
| WO | WO 00/50027 A1 | 8/2000 |
| WO | WO 00/064927 A1 | 11/2000 |
| WO | WO 00/29378 A3 | 12/2000 |
| WO | WO 00/73298 A1 | 12/2000 |
| WO | WO 00/78723 A1 | 12/2000 |
| WO | WO 01/03685 A2 | 1/2001 |
| WO | WO 01/03685 A3 | 1/2001 |
| WO | WO 01/05749 A1 | 1/2001 |
| WO | WO 01/05750 A1 | 1/2001 |
| WO | WO 01/05768 A1 | 1/2001 |
| WO | WO 01/05813 A1 | 1/2001 |
| WO | WO 01/07032 A1 | 2/2001 |
| WO | WO 01/10866 A1 | 2/2001 |
| WO | WO 01/28978 A1 | 4/2001 |
| WO | WO 01/30780 A2 | 5/2001 |
| WO | WO 01/30780 A3 | 5/2001 |
| WO | WO 01/40180 A2 | 6/2001 |
| WO | WO 01/40180 A3 | 6/2001 |
| WO | WO 01/42190 A1 | 6/2001 |
| WO | WO 01/42191 A1 | 6/2001 |
| WO | WO 01/54481 A2 | 8/2001 |
| WO | WO 01/55082 A2 | 8/2001 |
| WO | WO 01/56358 A2 | 8/2001 |
| WO | WO 01/62242 A1 | 8/2001 |
| WO | WO 01/70673 A2 | 9/2001 |
| WO | WO 01/70673 A3 | 9/2001 |
| WO | WO 01/85718 A1 | 11/2001 |
| WO | WO 01/90052 A1 | 11/2001 |

| | | |
|---|---|---|
| WO | WO 01/90081 A1 | 11/2001 |
| WO | WO 02/00584 A1 | 1/2002 |
| WO | WO 02/04458 A1 | 1/2002 |
| WO | WO 02/04459 A1 | 1/2002 |
| WO | WO 02/10120 A1 | 2/2002 |
| WO | WO 02/16315 A1 | 2/2002 |
| WO | WO 02/18327 A2 | 3/2002 |
| WO | WO 02/18327 A3 | 3/2002 |
| WO | WO 02/28411 A1 | 4/2002 |
| WO | WO 02/28827 A1 | 4/2002 |
| WO | WO 02/28881 A1 | 4/2002 |
| WO | WO 02/28883 A1 | 4/2002 |
| WO | WO 02/32376 A2 | 4/2002 |
| WO | WO 02/32376 A3 | 4/2002 |
| WO | WO 02/34698 A2 | 5/2002 |
| WO | WO 02/34698 A3 | 5/2002 |
| WO | WO 02/34711 A1 | 5/2002 |
| WO | WO 02/42414 A2 | 5/2002 |
| WO | WO 02/42414 A3 | 5/2002 |
| WO | WO 02/44324 A2 | 6/2002 |
| WO | WO 02/44324 A3 | 6/2002 |
| WO | WO 02/58680 A2 | 8/2002 |
| WO | WO 02/58680 A3 | 8/2002 |
| WO | WO 02/62766 A2 | 8/2002 |
| WO | WO 02/62766 A3 | 8/2002 |
| WO | WO 02/76980 A1 | 10/2002 |
| WO | WO 02/79189 A2 | 10/2002 |
| WO | WO 02/79189 A3 | 10/2002 |
| WO | WO 02/85855 | 10/2002 |
| WO | WO 02/85928 A2 | 10/2002 |
| WO | WO 02/85928 A3 | 10/2002 |
| WO | WO 02/88092 A1 | 10/2002 |
| WO | WO 02/87632 A1 | 11/2002 |
| WO | WO 02/92555 A1 | 11/2002 |
| WO | WO 02/94829 A1 | 11/2002 |
| WO | WO 02/100344 A2 | 12/2002 |
| WO | WO 02/100344 A3 | 12/2002 |
| WO | WO 03/00250 A1 | 1/2003 |
| WO | WO 03/00642 A2 | 1/2003 |
| WO | WO 03/00643 A1 | 1/2003 |
| WO | WO 03/05971 A2 | 1/2003 |
| WO | WO 03/09872 A1 | 2/2003 |
| WO | WO 03/30905 A1 | 4/2003 |
| WO | WO 03/35067 A1 | 5/2003 |
| WO | WO 03/40086 A1 | 5/2003 |

OTHER PUBLICATIONS

Alderman, "A Review of Cellulose Ethers in Hydrophilic Matrices for Oral Controlled-Release Dosage Forms," *Int. J. Pharm. Tech. & Prod. Mfr.* (1984) 5(3):1-9.

Alexander et al. Investigation of (Oxodioxolenyl)menthyl Carbamates as Nonchiral Bioreversible Prodrug Moieties for Chiral Amines, *Med. Chem.* (1996) 39,480-486.

Bamba et al., "Release Mechanisms in Gelforming Sustained Release Preparations" *Int. J. Pharm.* (1979) 2:307.

Butcher "Carbamate Esters: a Simple, Mild Method of Formation," *SynLett*, 1994, 825-826.

Coleman et al., "Polymer Review: A Practical Guide to Polymer Miscibility," *Polymers* 1990, 31, 1187-1231.

During et al., "Controlled Release of Dopamine From a Polymeric Brain Implant; In Vivo Characterization," *Ann. Neurol.* (1989) 25:351.

Fincher, "Particle Size of Drugs and Its Relationship to Absorption and Activity," *J. Pharm. Sci.* 1968, 57, 1825-1835.

Goodson, in "Medical Applications of Controlled Release," vol. 2, pp. 115-138 (1984) Langer and Wise (eds) CRC Press, Boca Raton, FLA.

Howard et al., "Intercerebral Drug Delivery in Rats with Lesion-Induced Memory Deficits," 1989, *J. Neurosurg.* 71:105-112.

Kayser et al., "Designer Yeast: an Enantioselective Oxidizing Reagent for Organic Synthesis." *SynLett* (1999) 1:153.

Langer, "Chemical and Physical Structure of Polymers as Carriers for Controlled Release of Bioactive Agents: A Review," *JMS—Rev Macromol. Chem Phys* (1983), C23(1): 61-126.

Langer, "New Methods of Drug Delivery," *Science* (1990) 249: 1527-1533.

Leong et al., "Polymeric Controlled Drug Delivery" *Adv. Drug Delivery Rev.* (1987) 1:199-233.

Levy et al., "Inhibition of Calcification of Bioprosthetic Heart Valves by Local Controlled-Release Diphosphonate," *Science* (1985) 228: 190-2.

Linhart, *Controlled Release of Drugs* Chap. 2, (1989) pp. 53-95.

Lu, "Dimensionless Presentation for Drug Release From A Coated Pure Drug Bead: 2. Experiment," *Int. J. Pharm.* (1994) 112, 117-124.

Magnus, "Nonepileptic Uses of Gabapentin," *Epilepsia*, (40) (Suppl. 6): S66-S72 (1999).

Peto et al., "The $TD_{50}$: A Proposed General Convention for the Numerical Description of the Carcinogenic Potency of Chemicals in Chronic-Exposure Animal Experiments," *Envir. Health Perspectives*, vol. 58, 1-8 (1984).

Renz et al., "100 years of Baeyer-Villiger Oxidations," *Eur. J. Org. Chem.* (1999) 737-750.

Roerdink et al., *Drug Carrier Systems* (1989) 9, 57-110.

Saudek et al., "A Preliminary Trial of the Programmable Implantable Medication System for Insulin Delivery," *N. Engl. J. Med.* (1989) 321:574-579.

Sefton "Implantable Pumps," *CRC Crit. Rev. Biomed. Eng.* (1987) 14(3): 201-240.

Stevenson et al., "Colonic Absorption of Antiepileptic Agents," (1997) *Epilepsia* 38(1): 63-7.

Stewart, "Cyclohexanone Monooxygenase: A Useful Reagent For Asymmetric Baeyer-Villiger Reactions," *Current Organic Chemistry* (1998) 2:195-216.

Strukul, "Transition Metal Catalysis in the Baeyer-Villiger Oxidation of Ketones," *Angnew. Chem. Int. Ed.* (1998) 37:1198-1209.

Sun et al., "A General Synthesis of Dioxolenone Prodrug Moieties," *Tetrahedron Letters* (2002) 1161-1164.

Verma et al., "Osmotically Controlled Oral Drug Delivery," *Drug Develop. Indus. Pharm.* (2000), 26(7): 695-708.

METHODS FOR SYNTHESIS OF ACYLOXYALKYL DERIVATIVES OF GABA ANALOGS

This application is a continuation-in-part of U.S. patent application Ser. No. 10/171,485, filed Jun. 11, 2002 now U.S. Pat. No. 6,818,787, which claimed the benefit under 35 U.S.C. § 119(e) from U.S. Provisional Application Ser. No. 60/297,521, filed Jun. 11, 2001; U.S. Provisional Application Ser. No. 60/298,514 filed Jun. 14, 2001; and U.S. Provisional Application Ser. No. 60/366,090 filed Mar. 19, 2002. The above applications are herein incorporated by reference in their entirety.

1. FIELD

Methods for synthesis of 1-(acyloxy)-alkyl carbamates are provided. More particularly, the synthesis of prodrugs (i.e., 1-(acyloxy)-alkyl carbamates of GABA analogs) from 1-haloalkyl carbamates of GABA analogs are described. Also described are new 1-haloalkyl carbamates of GABA analogs.

2. BACKGROUND

One solution to drug delivery and/or bioavailability issues in pharmaceutical development is converting known drugs to prodrugs. Typically, in a prodrug, a polar functional group (e.g., a carboxylic acid, an amino group, a hydroxyl group, etc.) is masked by a promoiety, which is labile under physiological conditions. Accordingly, prodrugs are usually transported through hydrophobic biological barriers such as membranes and typically possess superior physicochemical properties than the parent drug.

Pharmacologically effective prodrugs are non-toxic and are preferably selectively cleaved at the locus of drug action. Ideally, cleavage of the promoiety occurs rapidly and quantitatively with the formation of non-toxic by-products (i.e., the hydrolyzed promoiety).

The acyloxyalkoxycarbonyl functionality is an example of a promoiety that may be used to modulate the physiochemical properties of pharmaceuticals (Alexander, U.S. Pat. No. 4,916,230; Alexander, U.S. Pat. No. 5,733,907; Alexander et al., U.S. Pat. No. 4,426,391). Typically, 1-(acyloxy)-alkyl derivatives of a pharmaceutical possess superior bioavailability, may be less irritating to topical and gastric mucosal membranes and are usually more permeable through such membranes when compared to the parent drug.

However, although 1-(acyloxy)-alkyl ester derivatives of alcohols and 1-(acyloxy)-alkyl carbamate derivatives of amines have been frequently used to mask these polar functional groups in pharmaceuticals, existing synthetic methods for preparing these desirable derivatives are inadequate. Methods disclosed in the art for synthesis of acyloxyalkyl esters and carbamates are typically multi-step routes that utilize unstable intermediates and/or toxic compounds or salts and accordingly are difficult to perform on large scale (Alexander, U.S. Pat. No. 4,760,057; Lund, U.S. Pat. No. 5,401,868; Alexander, U.S. Pat. No. 4,760,057; Saari et al., European Patent 0416689B1).

Accordingly, there is a need for a new synthesis of 1-(acyloxy)-alkyl derivatives that proceeds rapidly and efficiently, which is amenable to scale-up and proceeds through readily accessible synthetic precursors.

3. SUMMARY

A method for synthesizing 1-(acyloxy)-alkyl derivatives from acyloxy derivatives, which typically proceeds in high yield, does not necessarily require the use of heavy metals and is readily amenable to scale-up is provided herein.

In a first aspect, a method of synthesizing a compound of Formula (I) is provided which comprises

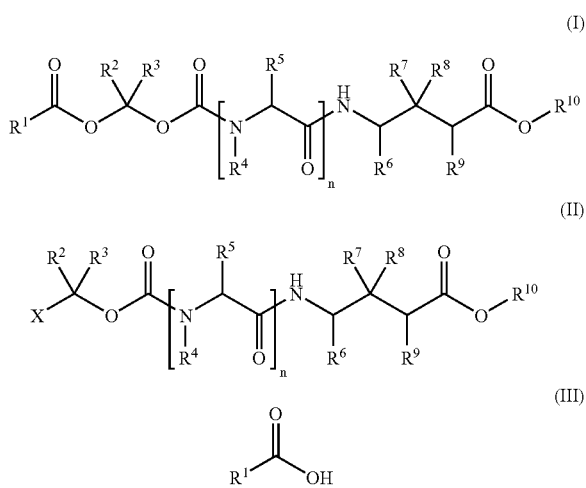

contacting a compound of Formula (II), a compound of Formula (III) and at least one equivalent of a metal salt wherein:

X is F, Cl, Br or I;

n is 0 or 1;

$R^1$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylakyl or substituted heteroarylalkyl;

$R^1$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or, optionally, $R^2$ and $R^3$ together with the atom to which they are bonded form a cycloalkyl, substituted cycloalkyl, cycloheteroalkyl or substituted cycloheteroalkyl ring;

$R^4$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^5$ is hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, or optionally, $R^4$ and $R^5$ together with the atoms to which they are attached form a cycloheteroalkyl or substituted cycloheteroalkyl ring;

$R^6$ and $R^9$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^7$ and $R^8$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, $R^7$ and $R^8$ together with the carbon atom to which they are attached form a cycloalkyl, substituted cycloalkyl, cycloheteroalkyl, substituted cycloheteroalkyl or bridged cycloalkyl ring; and $R^{10}$ is hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl.

In a second aspect a method of synthesizing a compound of Formula (I) is provided which comprises

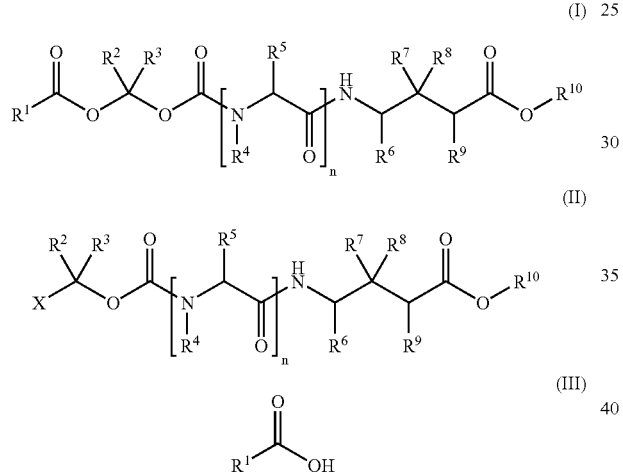

contacting a compound of Formula (II), a compound of Formula (III) and at least one equivalent of an organic base, where X, n, $R^1$, $R^2$, $R^3$, $R^4$, $R^5$, $R^6$, $R^7$, $R^8$, $R^9$ and $R^{10}$ are as defined, supra.

In a third aspect a compound of Formula (II) is provided,

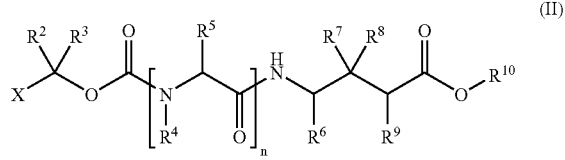

wherein:
X is F, Cl, Br or I;
n is 0 or 1;
$R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or optionally, $R^2$ and $R^3$ together with the atom to which they are bonded form a cycloalkyl, substituted cycloalkyl, cycloheteroalkyl, substituted cycloheteroalkyl or substituted cycloheteroalkyl ring;

$R^4$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^5$ is hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, or optionally, $R^4$ and $R^5$ together with the atoms to which they are attached form a cycloheteroalkyl or substituted cycloheteroalkyl ring;

$R^6$ and $R^9$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^7$ and $R^8$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, $R^7$ and $R^8$ together with the carbon atom to which they are attached form a cycloalkyl, substituted cycloalkyl, cycloheteroalkyl, substituted cycloheteroalkyl or bridged cycloalkyl ring; and $R^{10}$ is hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl.

4. DETAILED DESCRIPTION

4.1 Definitions

"Compounds" refers to compounds encompassed by structural formulae (I)–(VIII) disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"1-Acyloxy-Alkyl Carbamate" refers to an N-1-acyloxyalkoxycarbonyl derivative of a primary or secondary amine as encompassed by structural formulae (I), (V) and (VI) disclosed herein.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, most preferably, from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —OR$^{32}$ where R$^{32}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) and the aryl moiety is ($C_6$–$C_{20}$), more preferably, an arylalkyl group is ($C_6$–$C_{20}$) arylalkyl, e.g., the alkanyl, alkenyl or alkynyl moiety of the arylalkyl group is ($C_1$–$C_8$) and the aryl moiety is ($C_6$–$C_{12}$).

"Aryldialkylsilyl" by itself or as part of another substituent refers to the radical —SiR$^{33}$R$^{34}$R$^{35}$ where one of R$^{33}$, R$^{34}$ or R$^{35}$ is aryl as defined herein and the other two of R$^{33}$, R$^{34}$ or R$^{35}$ are alkyl as defined herein.

"Bridged cycloalkyl" by itself or as part of another substituent refers to a

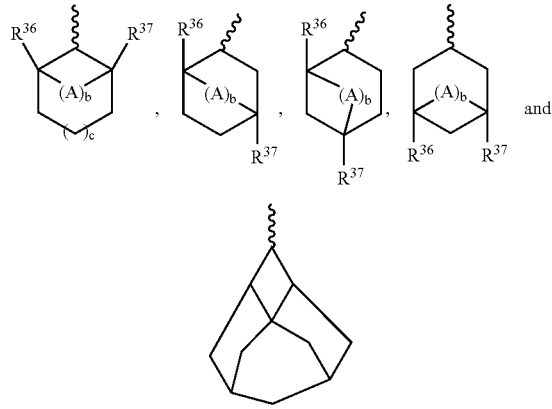

radical selected from the group consisting of wherein:

A is (CR$^{38}$R$^{39}$)$_b$;

R$^{38}$ and R$^{39}$ are independently selected from the group consisting of hydrogen and methyl;

R$^{36}$ and R$^{37}$ are independently selected from the group consisting of hydrogen and methyl;

b is an integer from 1 to 4; and c is an integer from 0 to 2.

"Carbamoyl" by itself or as part of another substituent refers to the radical —C(O)NR$^{40}$R$^{41}$ where R$^{40}$ and R$^{41}$ are independently hydrogen, alkyl, cycloalkyl or aryl as defined herein.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is (C$_3$–C$_{10}$) cycloalkyl, more preferably (C$_3$–C$_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"GABA analog" refers to a compound, unless specified otherwise, as having the following structure:

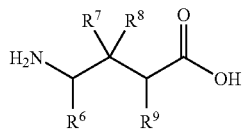

wherein:

R$^6$ and R$^9$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

R$^7$ and R$^8$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, R$^7$ and R$^8$ together with the carbon atom to which they are attached form a cycloalkyl, substituted cycloalkyl, cycloheteroalkyl, substituted cycloheteroalkyl or bridged cycloalkyl ring.

"1-Haloalkyl Carbamate" refers to an N-1-haloalkoxycarbonyl derivative of a primary or secondary amine as encompassed by structural formulae (II), (VII) and (VIII) disclosed herein.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{42}$R$^{43}$, =N—N=, —N=N—, —N=N—NR$^{44}$R$^{45}$, —PR$^{46}$—, —P(O)$_2$—, —POR$^{47}$—, —O—P(O)$_2$—, —SO—, —SO$_2$—, —SnR$^{48}$R$^{49}$— and the like, where R$^{42}$, R$^{43}$, R$^{44}$, R$^{45}$, R$^{46}$, R$^{47}$, R$^{48}$ and R$^{49}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5–20 membered heteroaryl, more preferably from 5–10 membered heteroaryl. Preferred heteroaryl groups are those derived from thiophene, pyrrole, benzothiophene, benzofuran, indole, pyridine, quinoline, imidazole, oxazole and pyrazine "Heteroarylalkyl" by itself or as part of another substituent refers to an acyclic alkyl radical in which one of the hydrogen atoms bonded to a carbon atom, typically a terminal or sp³ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl, more preferably, 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which have functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, —M, —$R^{60}$, —O⁻, =O, —$OR^{60}$, —$SR^{60}$, —S⁻, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —S(O)$_2$OH, —$S(O)_2R^{60}$, —$OS(O_2)O^-$, —$OS(O)_2R^{60}$, —P(O)(O⁻)$_2$, —P(O)($OR^{60}$)—(O⁻), —OP(O)($OR^{60}$)—($OR^{61}$), —$C(O)R^{60}$, —$C(S)R^{60}$, —$C(O)OR^{60}$, —$C(O)NR^{60}R^{61}$, —C(O)O⁻, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include —M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O_2)O^-$, —$OS(O)_2R^{60}$, —$P(O)(O^-)_2$, —$P(O)(OR^{60})(O^-)$, —OP(O)($OR^{60}$)($OR^{61}$), —$C(O)R^{60}$, —$C(S)R^{60}$, —$C(O)OR^{60}$, —$C(O)NR^{60}R^{61}$, —$C(O)O^-$, —$NR^{62}C(O)NR\ R^{61}$, more preferably, —M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$, most preferably, —M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above.

"Trialkylsilyl" by itself or as part of another substituent refers to a radical —$SiR^{50}R^{51}R^{52}$ where $R^{50}$, $R^{51}$ and $R^{52}$ are alkyl as defined herein.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

4.2. Method of Synthesis of 1-(Acyloxy)-Alkyl GABA Analogs

Methods of synthesis of 1-(acyloxy)-alkyl carbamates of GABA analogs from 1-haloalkyl carbamates of GABA analogs are disclosed. Preferably, 1-(acyloxy)-alkyl carbamates of GABA analogs are synthesized by reaction of a 1-haloalkyl carbamate of a GABA analog with a carboxylic acid in the presence of either a metal salt or an organic base. In one embodiment, the carboxylic acid also serves a solvent for the reaction.

In a first aspect, a compound of Formula (I) is synthesized by a method comprising

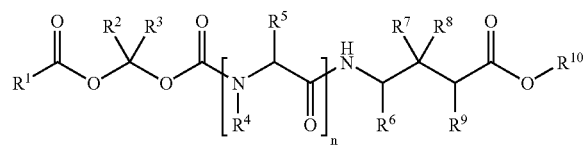

(I)

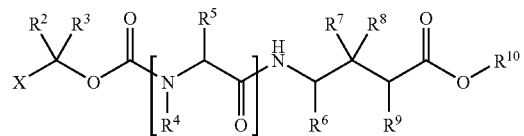

(II)

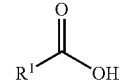

(III)

contacting a compound of Formula (II), a compound of Formula (III) and at least one equivalent of a metal salt wherein:

X is F, Cl, Br or I;

n is 0 or 1;

$R^1$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or optionally, $R^2$ and $R^3$ together with the atom to which they are bonded form a cycloalkyl, substituted cycloalkyl, cycloheteroalkyl or substituted cycloheteroalkyl ring;

$R^4$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^5$ is hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, or optionally, $R^4$ and $R^5$ together with the atoms to which they are attached form a cycloheteroalkyl or substituted cycloheteroalkyl ring;

$R^6$ and $R^9$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^7$ and $R^8$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, $R^7$ and $R^8$ together with the carbon atom to which they are attached form a cycloalkyl, substituted cycloalkyl, cycloheteroalkyl, substituted cycloheteroalkyl or bridged cycloalkyl ring; and $R^{10}$ is hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl.

In a second aspect, a compound of Formula (I) is synthesized by a method comprising contacting a compound of Formula (II), a compound of Formula (III) and at least one equivalent of an organic base, wherein X, n, $R^1$, $R^2$, $R^3$, $R^4$, $R^5$, $R^6$, $R^7$, $R^8$, $R^9$ and $R^{10}$ are as defined, supra.

Those of skill in the art will appreciate that many of the embodiments described, infra, are embodiments of both aspects, supra.

In one embodiment, $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl or substituted heteroaryl. In another embodiment, $R^2$ and $R^3$ are independently hydrogen, alkyl, alkoxycarbonyl, aryl, arylalkyl, carbamoyl, cycloalkyl, or heteroaryl. In still another embodiment, $R^2$ and $R^3$ are independently hydrogen, alkanyl or substituted alkanyl. In still another embodiment, $R^2$ and $R^3$ are independently hydrogen or alkanyl.

In still another embodiment, $R^1$ is alkyl, substituted alkyl, aryl, substituted aryl, arylalkyl, substituted arylalkyl, cycloalkyl, substituted cycloalkyl, heteroalkyl, substituted heteroalkyl, heteroaryl or substituted heteroaryl. In still another embodiment, $R^1$ is alkyl or substituted alkyl. In still another embodiment, $R^1$ is alkanyl or substituted alkanyl.

In still another embodiment, $R^1$ is alkyl, substituted alkyl, aryl, substituted aryl, arylalkyl, substituted arylalkyl, cycloalkyl, substituted cycloalkyl, heteroalkyl, substituted heteroalkyl, heteroaryl or substituted heteroaryl, and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl, substituted heteroaryl, heteroarylalkyl or substituted heteroarylalkyl. In still another embodiment, $R^1$ is alkyl, substituted alkyl, aryl, arylalkyl or heteroaryl and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl, substituted heteroaryl, heteroarylalkyl or substituted heteroarylalkyl. In still another embodiment, $R^1$ is alkanyl or substituted alkanyl and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl, substituted heteroaryl, heteroarylalkyl or substituted heteroarylalkyl.

In still another embodiment, $R^1$ is alkyl, substituted alkyl, aryl, substituted aryl, arylalkyl, substituted arylalkyl, cycloalkyl or substituted cycloalkyl and $R^2$ and $R^3$ are independently hydrogen, alkyl, alkoxycarbonyl, aryl, arylalkyl, carbamoyl, cycloalkyl or heteroaryl. In still another embodiment, $R^1$ is alkyl, substituted alkyl, aryl, substituted aryl, arylalkyl, substituted arylalkyl, cycloalkyl or substituted cycloalkyl and $R^2$ and $R^3$ are independently hydrogen, alkanyl or substituted alkanyl. In still another embodiment, $R^1$ is alkyl, substituted alkyl, aryl, substituted aryl, arylalkyl, substituted arylalkyl, cycloalkyl or substituted cycloalkyl and $R^2$ and $R^3$ are independently alkanyl.

In still another embodiment, $R^1$ is alkyl, substituted alkyl, aryl, substituted aryl, arylalkyl, substituted arylalkyl, cycloalkyl, substituted cycloalkyl, heteroaryl or substituted heteroaryl and $R^2$ and $R^3$ together with the atom to which they are attached form a cycloalkyl, substituted cycloalkyl, cycloheteroalkyl or substituted cycloheteroalkyl ring. In still another embodiment, $R^1$ is alkyl, substituted alkyl, aryl, arylalkyl, cycloalkyl or heteroaryl and $R^2$ and $R^3$ are independently hydrogen, alkyl, alkoxycarbonyl, aryl, arylalkyl, carbamoyl, cycloalkyl or heteroaryl. In still another embodiment, $R^1$ is alkyl, substituted alkyl, aryl, arylalkyl, cycloalkyl or heteroaryl and $R^2$ and $R^3$ are independently hydrogen, alkanyl or substituted alkanyl. In still another embodiment, $R^1$ is alkyl, substituted alkyl, aryl, arylalkyl, cycloalkyl or heteroaryl and $R^2$ and $R^3$ are independently alkanyl. In still another embodiment, $R^1$ is alkyl, substituted alkyl, aryl, arylalkyl, cycloalkyl or heteroaryl and $R^2$ and $R^3$ together with the atom to which they are attached form a cycloalkyl, substituted cycloalkyl, cycloheteroalkyl or substituted cycloheteroalkyl ring.

In still another embodiment, $R^1$ is alkanyl or substituted alkanyl and $R^2$ and $R^3$ are independently hydrogen, alkyl, alkoxycarbonyl, aryl, arylalkyl, carbamoyl, cycloalkyl or heteroaryl. In still another embodiment, $R^1$ is alkanyl or substituted alkanyl and $R^2$ and $R^3$ are independently hydrogen, alkanyl or substituted alkanyl. In still another embodiment, $R^1$ is alkanyl or substituted alkanyl and $R^2$ and $R^3$ are independently alkanyl. In still another embodiment, $R^1$ is alkanyl or substituted alkanyl, and $R^2$ and $R^3$ together with the atom to which they are attached form a cycloalkyl, substituted cycloalkyl, cycloheteroalkyl or substituted cycloheteroalkyl ring.

In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl.

In still another embodiment, $R^2$ and $R^3$ are independently hydrogen, methyl, ethyl, propyl, isopropyl, butyl, isobutyl, sec-butyl, tert-butyl, cyclobutyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl and $R^2$ and $R^3$ are independently hydrogen, methyl, ethyl, propyl, isopropyl, butyl, isobutyl, sec-butyl, tert-butyl, cyclobutyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl and $R^2$ and $R^3$ together with the atom to which they are attached form a cyclobutyl, cyclopentyl or cyclohexyl ring.

In still another embodiment, $R^2$ is methyl, ethyl, propyl, isopropyl, butyl, isobutyl, sec-butyl, tert-butyl, cyclohexyl or phenyl and $R^3$ is hydrogen. In still another embodiment, $R^2$ is methyl, methoxycarbonyl, ethoxycarbonyl, isopropoxycarbonyl or cyclohexyloxycarbonyl and $R^3$ is methyl.

In still another embodiment, $R^1$ is methyl, ethyl, n-propyl, isopropyl, n-butyl, isobutyl, sec-butyl, tert-butyl, 1,1-dimethoxyethyl or 1,1-diethoxyethyl. In still another embodiment, $R^2$ is methyl, ethyl, n-propyl, isopropyl, n-butyl, isobutyl, sec-butyl or tert-butyl, and $R^3$ is hydrogen. In still another embodiment, $R^1$ is methyl, ethyl, n-propyl, isopropyl, n-butyl, isobutyl, sec-butyl, tert-butyl, 1,1-dimethoxyethyl or 1,1-diethoxyethyl, $R^2$ is methyl, ethyl, n-propyl, isopropyl, n-butyl, isobutyl, sec-butyl or tert-butyl, and $R^3$ is hydrogen.

In still another embodiment, $R^{10}$ is hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl. In still another embodiment, $R^{10}$ is hydrogen. In still another embodiment, $R^{10}$ is alkanyl, substituted alkanyl, alkenyl, substituted alkenyl, aryl, substituted aryl, arylalkyl, substituted arylalkyl, aryldialkylsilyl or trialkylsilyl. In still another embodiment, $R^{10}$ is methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl, phenyldimethylsilyl, —C(CH$_3$)=CH$_2$, —CH$_2$C(O)N(CH$_3$)$_2$,

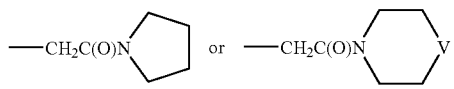

where V is —O— or —CH$_2$—.

In one embodiment, n is 0. In another embodiment, n is 1.

In one embodiment, $R^5$ is selected from the group consisting of hydrogen, alkanyl, substituted alkanyl, aryl, substituted aryl, arylalkanyl, substituted arylalkanyl, cycloalkanyl, heteroarylalkyl and substituted heteroarylalkanyl. In another embodiment, $R^5$ is selected from the group consisting of hydrogen, alkanyl and cycloalkanyl. In still another embodiment, $R^5$ is selected from the group consisting of hydrogen, methyl, isopropyl, isobutyl, sec-butyl, tert-butyl, cyclopentyl and cyclohexyl. In still another embodiment, $R^5$ is selected from the group consisting of substituted alkanyl. In still another embodiment, $R^5$ is selected from the group consisting of —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ and —CH$_2$CH$_2$CH$_2$NHC(NH)NH$_2$. In still another embodiment, $R^5$ is selected from the group consisting of aryl, arylalkanyl, substituted arylalkanyl and heteroarylalkanyl. In still another embodiment, $R^5$ is selected from the group consisting of phenyl, benzyl, 4-hydroxybenzyl, 4-bromobenzyl, 4-imidazolylmethyl and 3-indolylmethyl.

In still another embodiment, $R^4$ and $R^5$ together with the atoms to which they are attached form a cycloheteroalkyl or substituted cycloheteroalkyl ring. In still another embodiment, $R^4$ and $R^5$ together with the atoms to which they are attached form an azetidine, pyrrolidine or piperidine ring.

In one embodiment, $R^6$ and $R^9$ are independently selected from the group consisting of hydrogen, alkyl, substituted alkyl, aryl, substituted aryl, cycloalkyl and substituted cycloalkyl. In another embodiment, $R^6$ and $R^9$ are independently selected from the group consisting of hydrogen and alkanyl. In still another embodiment, $R^6$ and $R^9$ are both hydrogen.

In one embodiment, $R^7$ and $R^8$ are independently selected from the group consisting of hydrogen, alkyl, substituted alkyl, cycloalkyl, substituted cycloalkyl, cycloheteroalkyl and substituted cycloheteroalkyl. In another embodiment, $R^7$ and $R^8$ are independently selected from the group consisting of hydrogen, alkanyl and substituted alkanyl. In still another embodiment, $R^7$ is hydrogen and $R^8$ is selected from the group consisting of $C_{1-6}$ alkanyl.

In still another embodiment, $R^7$ and $R^8$ together with the carbon atom to which they are attached are cycloalkanyl or substituted cycloalkanyl. In still another embodiment, $R^7$ and $R^8$ together with the carbon atom to which they are attached are selected from the group consisting of cyclobutyl, substituted cyclobutyl, cyclopentyl, substituted cyclopentyl, cyclohexyl and substituted cyclohexyl.

In still another embodiment, $R^7$ and $R^8$ together with the carbon atom to which they are attached are cycloheteroalkyl or substituted cycloheteroalkyl. In still another embodiment, $R^7$ and $R^8$ together with the carbon atom to which they are attached are bridged cycloalkyl.

In one embodiment, X is chloro, bromo or iodo. In another embodiment, X is chloro, and $R^2$ and $R^3$ are independently hydrogen or alkanyl. In still another embodiment, X is chloro, and $R^2$ and $R^1$ together with the atom to which they are attached form a cycloalkanyl ring. In still another embodiment, X is chloro, bromo or iodo, and $R^2$ and $R^3$ are independently hydrogen, methyl, ethyl, propyl, isopropyl, butyl, isobutyl, sec-butyl, tert-butyl, cyclobutyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl. In still another embodiment, X is chloro, bromo or iodo, and $R^2$ and $R^3$ together with the atom to which they are attached form a cyclobutyl, cyclopentyl or cyclohexyl ring. In still another embodiment, X is chloro, bromo or iodo, $R^2$ is methyl, ethyl, n-propyl, isopropyl, n-butyl, isobutyl, sec-butyl, tert-butyl, cyclohexyl or phenyl and $R^3$ is hydrogen.

In one embodiment, a compound of Formulae (I) or (II) is derived is derived from a GABA analog of Formula (IV):

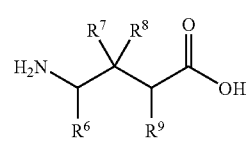

(IV)

wherein the GABA analog of Formula (IV) is selected from the group consisting of:

1-Aminomethyl-1-cyclohexane acetic acid (i.e. gabapentin);
1-Aminomethyl-1-(3-methylcyclohexane) acetic acid;
1-Aminomethyl-1-(4-methylcyclohexane) acetic acid;
1-Aminomethyl-1-(4-isopropylcyclohexane) acetic acid;
1-Aminomethyl-1-(4-tert-butylcyclohexane) acetic acid;
1-Aminomethyl-1-(3,3-dimethylcyclohexane) acetic acid;
1-Aminomethyl-1-(3,3,5,5-tetramethylcyclohexane) acetic acid;
1-Aminomethyl-1-cyclopentane acetic acid;
1-Aminomethyl-1-(3-methylcyclopentane) acetic acid;

1-Aminomethyl-1-(3,4-dimethylcyclopentane) acetic acid;
7-Aminomethyl-bicyclo[2.2.1]hept-7-yl acetic acid;
9-Aminomethyl-bicyclo[3.3.1]non-9-yl acetic acid;
4-Aminomethyl-4-(tetrahydropyran-4-yl) acetic acid;
3-Aminomethyl-3-(tetrahydropyran-3-yl) acetic acid;
4-Aminomethyl-4-(tetrahydrothiopyran-4-yl) acetic acid;
3-Aminomethyl-3-(tetrahydrothiopyran-3-yl) acetic acid;
(S)-3-Aminomethyl-5-methyl-hexanoic acid (i.e. pregabalin);
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-phenyl-hexanoic acid;
3-Aminomethyl-5-phenyl-pentanoic acid;
3-Aminomethyl-4-cyclobutyl-butyric acid;
3-Aminomethyl-4-cyclopentyl-butyric acid;
3-Aminomethyl-4-cyclohexyl-butyric acid;
3-Aminomethyl-4-phenoxy-butyric acid;
3-Aminomethyl-5-phenoxy-hexanoic acid; and
3-Aminomethyl-5-benzylsulfanyl-pentanoic acid.

In another embodiment, the compound of Formula (I) is a compound of Formulae (V) or (VI):

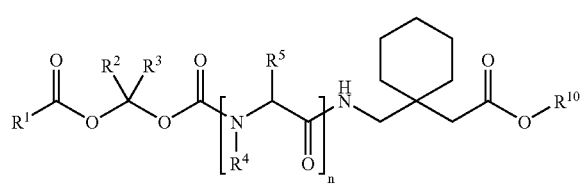

(V)

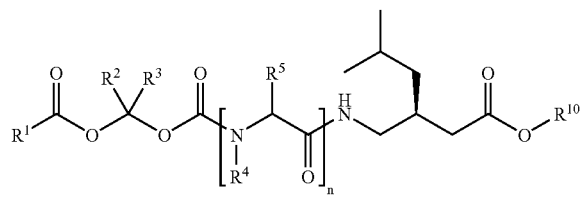

(VI)

The skilled artisan will appreciate that the embodiments, infra, refer to compounds of Formulae (V) and (VI) In one embodiment, n is 0. In another embodiment n is 1.

In one embodiment, $R^5$ is selected from the group consisting of hydrogen, alkanyl, substituted alkanyl, aryl, substituted aryl, arylalkanyl, substituted arylalkanyl, cycloalkanyl, heteroarylalkyl and substituted heteroarylalkanyl. In another embodiment, $R^5$ is selected from the group consisting of hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ and —CH$_2$CH$_2$CH$_2$NHC(NH)NH$_2$, phenyl, benzyl, 4-hydroxybenzyl, 4-bromobenzyl, 4-imidazolylmethyl and 3-indolylmethyl.

In still another embodiment, $R^4$ and $R^5$ together with the atoms to which they are attached form a cycloheteroalkyl or substituted cycloheteroalkyl ring. In still another embodiment, $R^4$ and $R^5$ together with the atoms to which they are attached form an azetidine, pyrrolidine or piperidine ring.

In one embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is hydrogen and $R^3$ is hydrogen. In another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is methyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is ethyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is propyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is isopropyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is butyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is isobutyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is sec-butyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is tert-butyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is cyclohexyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is phenyl and $R^3$ is hydrogen. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is methyl and $R^3$ is methyl. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is methoxycarbonyl and $R^3$ is methyl. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is ethoxycarbonyl and $R^3$ is methyl. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is isopropoxycarbonyl and $R^3$ is methyl. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is cyclohexyloxycarbonyl and $R^3$ is methyl. In still another embodiment, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl and $R^2$ and $R^3$ together with the atom to which they are attached form a cyclohexyl ring.

In one embodiment, $R^2$ is methyl, methoxycarbonyl, ethoxycarbonyl, isopropoxycarbonyl or cyclohexyloxycarbonyl and $R^3$ is methyl. In another embodiment, $R^2$ is hydrogen, methyl, ethyl, n-propyl, isopropyl, n-butyl, isobutyl, sec-butyl or tert-butyl and $R^3$ is hydrogen.

In one embodiment, $R^1$ is methyl, ethyl, n-propyl, isopropyl, n-butyl, isobutyl, sec-butyl, tert-butyl, 1,1-dimethoxyethyl, 1,1-diethoxyethyl, cyclobutyl, cyclopentyl or cyclohexyl, and $R^{10}$ is hydrogen, allyl, benzyl or trimethylsilyl.

In one embodiment, $R^1$ is methyl, ethyl, n-propyl, isopropyl, n-butyl, isobutyl, sec-butyl, tert-butyl, 1,1-dimethoxyethyl, 1,1-diethoxyethyl, cyclobutyl, cyclopentyl or cyclohexyl, $R^{10}$ is hydrogen, allyl, benzyl or trimethylsilyl, $R^2$ is hydrogen, methyl, ethyl, isopropyl, n-butyl, isobutyl, sec-butyl or tert-butyl, and $R^3$ is hydrogen. In another embodiment, $R^1$ is ethyl or isopropyl, $R^{10}$ is allyl, benzyl or trimethylsilyl, $R^2$ is methyl, n-propyl or isopropyl, and $R^3$ is hydrogen. In still another embodiment, $R^1$ is isopropyl, $R^1$ is benzyl, $R^2$ is methyl, and $R^3$ is hydrogen. In still another embodiment, $R^1$ is isopropyl, $R^{10}$ is allyl, $R^2$ is methyl, and $R^3$ is hydrogen.

In one embodiment, $R^1$ is ethyl or isopropyl, $R^{10}$ is allyl, benzyl or trimethylsilyl, $R^2$ is methyl, n-propyl or isopropyl, $R^3$ is hydrogen and X is chloro. In another embodiment, $R^1$ is isopropyl, $R^{10}$ is benzyl, $R^2$ is methyl, $R^3$ is hydrogen and X is chloro. In still another embodiment, $R^1$ is isopropyl, $R^{10}$ is allyl, $R^2$ is methyl, $R^3$ is hydrogen and X is chloro.

In one embodiment, X is bromo or chloro. In another embodiment, X is chloro, bromo or iodo, $R^{10}$ is hydrogen, allyl, benzyl or trimethylsilyl, $R^2$ is hydrogen and $R^3$ is hydrogen. In still another embodiment, X is chloro, bromo or iodo, $R^{10}$ is hydrogen, allyl, benzyl or trimethylsilyl, $R^2$ is methyl and $R^3$ is hydrogen. In still another embodiment, X is chloro, bromo or iodo, $R^{10}$ is hydrogen, allyl, benzyl or trimethylsilyl, $R^2$ is ethyl and $R^3$ is hydrogen. In still another embodiment, X is chloro, bromo or iodo, $R^{10}$ is hydrogen, allyl, benzyl or trimethylsilyl, $R^2$ is propyl and $R^3$ is hydrogen. In still another embodiment, X is chloro, bromo or iodo, $R^{10}$ is hydrogen, allyl, benzyl or trimethylsilyl, $R^2$ is isopropyl and $R^3$ is hydrogen. In still another embodiment, X is chloro, bromo or iodo, $R^{10}$ is hydrogen, allyl, benzyl or trimethylsilyl, $R^2$ is butyl and $R^3$ is hydrogen. In still another embodiment, X is chloro, bromo or iodo, $R^{10}$ is hydrogen, allyl, benzyl or trimethylsilyl, $R^2$ is isobutyl and $R^3$ is hydrogen. In still another embodiment, X is chloro, bromo or iodo, $R^{10}$ is hydrogen, allyl, benzyl or trimethylsilyl, $R^2$ is sec-butyl and $R^3$ is hydrogen. In still another embodiment, X is chloro, bromo or iodo, $R^{10}$ is hydrogen, allyl, benzyl or trimethylsilyl, $R^2$ is tert-butyl and $R^3$ is hydrogen. In still another embodiment, X is chloro, bromo or iodo, $R^{10}$ is hydrogen, allyl, benzyl or trimethylsilyl, $R^2$ is cyclohexyl and $R^3$ is hydrogen. In still another embodiment, X is chloro, bromo or iodo, $R^{10}$ is hydrogen, allyl, benzyl or trimethylsilyl, $R^2$ is phenyl and $R^3$ is hydrogen. In still another embodiment, X is chloro, bromo or iodo, $R^{10}$ is hydrogen, allyl, benzyl or trimethylsilyl, $R^2$ is methyl and $R^3$ is methyl. In still another embodiment, X is chloro, bromo or iodo, $R^{10}$ is hydrogen, allyl, benzyl or trimethylsilyl, $R^2$ is methoxycarbonyl and $R^3$ is methyl. In still another embodiment, X is chloro, bromo or iodo, $R^{10}$ is hydrogen, allyl, benzyl or trimethylsilyl, $R^2$ is ethoxycarbonyl and $R^3$ is methyl. In still another embodiment, X is chloro, bromo or iodo, $R^{10}$ is hydrogen, allyl, benzyl or trimethylsilyl, $R^2$ is isopropoxycarbonyl and $R^3$ is methyl. In still another embodiment, X is chloro, bromo or iodo, $R^1$ is hydrogen, allyl, benzyl or trimethylsilyl, $R^2$ is cyclohexyloxycarbonyl and $R^3$ is methyl. In still another embodiment, X is chloro, bromo or iodo, $R^{10}$ is hydrogen, allyl, benzyl or trimethylsilyl and $R^2$ and $R^3$ together with the atom to which they are attached form a cyclohexyl ring. In still another embodiment, X is chloro, $R^{10}$ is hydrogen, allyl, benzyl or trimethylsilyl, $R^2$ is hydrogen, methyl, ethyl, n-propyl, isopropyl, n-butyl, isobutyl, sec-butyl or tert-butyl and $R^3$ is hydrogen. In still another embodiment, X is chloro, $R^{10}$ is hydrogen, allyl, benzyl or trimethylsilyl, $R^2$ is methyl, n-propyl or isopropyl, and $R^3$ is hydrogen. In still another embodiment, X is chloro, $R^{10}$ is allyl, $R^2$ is methyl, and $R^3$ is hydrogen. In still another embodiment, X is chloro, $R^{10}$ is benzyl, $R^2$ is methyl, and $R^3$ is hydrogen. In still another embodiment, X is chloro, $R^{10}$ is trimethylsilyl, $R^2$ is methyl, and $R^3$ is hydrogen.

Those of skill in the art will appreciate that the following embodiments, infra, refer to compounds of Formulae (I), (II) and (III). In one embodiment, the ratio of the compound of Formula (II) to the compound of Formula (III) is between about 1:1 and 1:20. In another embodiment, the ratio of the compound of Formula (II) to the compound of Formula (III) is between about 1:1 and 1:5. In still another embodiment, the ratio of the compound of Formula (II) to the compound of Formula (III) is about 1:1.

In one embodiment, the compounds of Formulae (II) and (III) and the metal salt are contacted with a solvent. In another embodiment, the ratio of the compound of Formula (II) to the compound of Formula (III) is between about 1:1 and 1:20. In still another embodiment, the ratio of the compound of Formula (II) to the compound of Formula (III) is between about 1:1 and 1:5. In still another embodiment, the ratio of the compound of Formula (II) to the compound of Formula (III) is about 1:1. In one embodiment, the solvent is dichloromethane, dichloroethane, chloroform, toluene, dimethylformamide, dimethylacetamide, N-methylpyrrolidinone, dimethyl sulfoxide, pyridine, ethyl acetate, acetonitrile, acetone, 2-butanone, methyl tert-butyl ether, methanol, ethanol, isopropanol, tert-butanol, water, hexamethylphosphoramide or combinations thereof. In another embodiment, the metal is Ag, Hg, Na, K, Li, Cs, Ca, Mg or Zn.

In one embodiment, the compounds of Formulae (II) and (III) and the organic base are contacted with a solvent. In another embodiment, the ratio of the compound of Formula (II) to the compound of Formula (III) is between about 1:1 and 1:20. In still another embodiment, the ratio of the compound of Formula (II) to the compound of Formula (III) is between about 1:15 and 1:20. In still another embodiment, the ratio of the compound of Formula (II) to the compound of Formula (III) is about 1:10. In still another embodiment, the ratio of the compound of Formula (II) to the compound of Formula (III) is between about 1:1 and 1:5. In still another embodiment, the ratio of the compound of Formula (II) to the compound of Formula (III) is about 1:1. In one embodiment, the solvent is dichloromethane, dichloroethane, chloroform, toluene, dimethylformamide, dimethylacetamide, N-methylpyrrolidinone, dimethyl sulfoxide, pyridine, ethyl acetate, acetonitrile, acetone, 2-butanone, methyl tert-butyl ether, methanol, ethanol, isopropanol, tert-butanol, water, hexamethylphosphoramide or combinations thereof. In another embodiment, the organic base is triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, 1,5-diazabicyclo[4.3.0]undec-7-ene or combinations thereof.

In one embodiment, the compound of Formula (III) is a liquid under the conditions of said contacting, the compound of Formula (III) further serving as a solvent for the reaction with the compound of Formula (II). In another embodiment, the compound of Formula (III) is acetic acid, methoxyacetic acid, ethoxyacetic acid, propionic acid, butyric acid, isobutyric acid, pivalic acid, valeric acid, isovaleric acid, 2-methylbutyric acid, cyclobutanecarboxylic acid, cyclopentanecarboxylic acid or cyclohexanecarboxylic acid. In still another embodiment, the compound of Formula (III) is isobutyric acid.

In one embodiment, the compound of Formula (II), the compound of Formula (III) and the metal salt are contacted at a temperature between about −25° C. and about 120° C. In another embodiment, the temperature is between about 0° C. and about 25° C.

In one embodiment, the compound of Formula (II), the compound of Formula (III) and the organic base are contacted at a temperature between about −25° C. and about 120° C. In another embodiment, the temperature is between about 0° C. and about 25° C.

In one embodiment, the compound of Formula (II), the compound of Formula (III) and the organic base are contacted with a catalytic amount of an iodide salt. In still another embodiment, the iodide salt is sodium iodide, potassium iodide, tetramethylammonium iodide, tetraethylammonium iodide or tetrabutylammonium iodide.

4.3 1-Haloalkyl Carbamates of GABA Analogs

Also disclosed herein are 1-haloalkyl carbamates of GABA analogs of Formula (II):

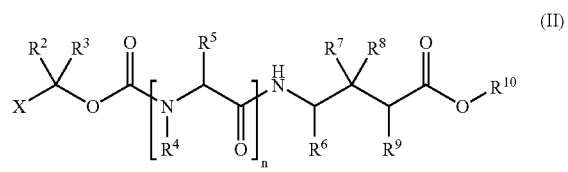

wherein:
X is a halogen;
n is 0 or 1;
$R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or optionally, $R^2$ and $R^3$ together with the atom to which they are bonded form a cycloalkyl, substituted cycloalkyl, cycloheteroalkyl or substituted cycloheteroalkyl ring;
$R^4$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;
$R^5$ is hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, or optionally, $R^4$ and $R^5$ together with the atoms to which they are attached form a cycloheteroalkyl or substituted cycloheteroalkyl ring;
$R^6$ and $R^9$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;
$R^7$ and $R^8$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, $R^7$ and $R^8$ together with the carbon atom to which they are attached form a cycloalkyl, substituted cycloalkyl, cycloheteroalkyl, substituted cycloheteroalkyl or bridged cycloalkyl ring; and
$R^{10}$ is hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl.

Those of skill in the art will appreciate that the following embodiments, infra, refer to compounds of Formula (II). In one embodiment, $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl or substituted heteroaryl. In another embodiment, $R^2$ and $R^3$ are independently hydrogen, alkyl, alkoxycarbonyl, aryl, arylalkyl, carbamoyl, cycloalkyl or heteroaryl. In still another embodiment, $R^2$ and $R^3$ are independently hydrogen, alkanyl or substituted alkanyl. In still another embodiment, $R^2$ and $R^3$ are independently hydrogen or alkanyl. In still another embodiment, $R^2$ and $R^3$ together with the atom to which they are bonded form a cycloalkyl, substituted cycloalkyl, cycloheteroalkyl or substituted cycloheteroalkyl ring. In still another embodiment $R^2$ and $R^3$ together with the atom to which they are bonded form a cycloalkanyl ring.

In one embodiment, X is chloro, bromo or iodo. In another embodiment, X is chloro.

In one embodiment, X is chloro, bromo or iodo and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl, substituted heteroaryl, heteroarylalkyl or substituted heteroarylalkyl. In another embodiment, X is chloro, bromo or iodo, and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl, substituted heteroaryl, heteroarylalkyl or substituted heteroarylalkyl. In still another embodiment, X is chloro and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl, substituted heteroaryl, heteroarylalkyl or substituted heteroarylalkyl.

In still another embodiment, X is chloro, bromo or iodo, and $R^2$ and $R^3$ are independently hydrogen, alkyl, alkoxycarbonyl, aryl, arylalkyl, carbamoyl, cycloalkyl or heteroaryl. In another embodiment, X is chloro, bromo or iodo, and $R^2$ and $R^3$ are independently hydrogen, alkanyl or substituted alkanyl. In still another embodiment, X is chloro, bromo or iodo, and $R^2$ and $R^3$ are independently alkanyl. In still another embodiment, X is chloro, bromo or iodo, and $R^2$ and $R^3$ together with the atom to which they are attached form a cycloalkyl, substituted cycloalkyl, cycloheteroalkyl or substituted cycloheteroalkyl ring.

In still another embodiment, X is chloro, and $R^2$ and $R^3$ are independently hydrogen, alkyl, alkoxycarbonyl, aryl, arylalkyl, carbamoyl, cycloalkyl or heteroaryl. In still another embodiment, X is chloro, and $R^2$ and $R^3$ are independently hydrogen, alkanyl or substituted alkanyl. In still another embodiment, X is chloro, and $R^2$ and $R^3$ are independently alkanyl. In still another embodiment, X is chloro, and $R^2$ and $R^3$ together with the atom to which they are attached form a cycloalkanyl ring.

In one embodiment, $R^2$ and $R^3$ are independently hydrogen, methyl, ethyl, propyl, isopropyl, butyl, isobutyl, sec-butyl, tert-butyl, cyclobutyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In another embodiment, X is chloro, bromo or iodo, and $R^2$ and $R^3$ are independently hydrogen, methyl, ethyl, propyl, isopropyl, butyl, isobutyl, sec-butyl, tert-butyl, cyclobutyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl. In still another embodiment, X is chloro, bromo or iodo, and $R^2$ and $R^3$ together with the atom to which they are attached form a cyclobutyl, cyclopentyl or cyclohexyl ring.

In one embodiment, $R^2$ is methyl, ethyl, n-propyl, isopropyl, n-butyl, isobutyl, sec-butyl, tert-butyl, cyclohexyl or phenyl and $R^3$ is hydrogen. In another embodiment, $R^2$ is methyl, methoxycarbonyl, ethoxycarbonyl, isopropoxycarbonyl or cyclohexyloxycarbonyl and $R^3$ is methyl.

In still another embodiment, X is chloro, bromo or iodo, $R^2$ is methyl, ethyl, n-propyl, isopropyl, n-butyl, isobutyl, sec-butyl, tert-butyl, cyclohexyl or phenyl and $R^3$ is hydrogen.

In one embodiment, $R^{10}$ is hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl. In another embodiment, $R^{10}$ is hydrogen. In still another embodiment, $R^{10}$ is alkanyl, substituted alkanyl, alkenyl, substituted alkenyl, aryl, substituted aryl, arylalkyl, substituted arylalkyl, aryldialkylsilyl or trialkylsilyl. In still another embodiment, $R^{10}$ is methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl, phenyldimethylsilyl, —C(CH$_3$)=CH$_2$, —CH$_2$C(O)N(CH$_3$)$_2$,

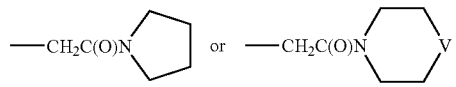

where V is —O— or —CH$_2$—. In still another embodiment, $R^{10}$ is allyl. In still another embodiment, $R^{10}$ is benzyl. In still another embodiment, $R^{10}$ is trimethylsilyl.

In one embodiment, n is 0. In another embodiment, n is 1.

In one embodiment, $R^4$ is hydrogen. In another embodiment, $R^5$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl. In another embodiment, $R^5$ is selected from the group consisting of hydrogen, alkanyl and cycloalkanyl. In still another embodiment, $R^5$ is selected from the group consisting of hydrogen, methyl, isopropyl, isobutyl, sec-butyl, tert-butyl, cyclopentyl and cyclohexyl. In still another embodiment, $R^5$ is selected from the group consisting of substituted alkanyl. In still another embodiment, $R^5$ is selected from the group consisting of —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ and —CH$_2$CH$_2$CH$_2$NHC(NH)NH$_2$. In still another embodiment, $R^5$ is selected from the group consisting of aryl, arylalkanyl, substituted arylalkanyl and heteroarylalkanyl. In still another embodiment, $R^5$ is selected from the group consisting of phenyl, benzyl, 4-hydroxybenzyl, 4-bromobenzyl, 4-imidazolylmethyl and 3-indolylmethyl.

In still another embodiment, $R^4$ and $R^5$ together with the atoms to which they are attached form a cycloheteroalkyl or substituted cycloheteroalkyl ring. In still another embodiment, $R^4$ and $R^5$ together with the atoms to which they are attached form an azetidine, pyrrolidine or piperidine ring.

In one embodiment, $R^6$ and $R^9$ are independently selected from the group consisting of hydrogen, alkyl, substituted alkyl, aryl, substituted aryl, cycloalkyl and substituted cycloalkyl. In another embodiment, $R^6$ and $R^9$ are independently selected from the group consisting of hydrogen and alkanyl. In still another embodiment, $R^6$ and $R^9$ are both hydrogen.

In one embodiment, $R^7$ and $R^8$ are independently selected from the group consisting of hydrogen, alkyl, substituted alkyl, cycloalkyl, substituted cycloalkyl, cycloheteroalkyl and substituted cycloheteroalkyl. In another embodiment, $R^7$ and $R^8$ are independently selected from the group consisting of hydrogen, alkanyl and substituted alkanyl. In still another embodiment, $R^7$ is hydrogen and $R^8$ is selected from the group consisting of $C_{1-6}$ alkanyl.

In still another embodiment, $R^7$ and $R^8$ together with the carbon atom to which they are attached are cycloalkanyl or substituted cycloalkanyl. In still another embodiment, $R^7$ and $R^8$ together with the carbon atom to which they are attached are selected from the group consisting of cyclobutyl, substituted cyclobutyl, cyclopentyl, substituted cyclopentyl, cyclohexyl and substituted cyclohexyl. In still another embodiment, $R^7$ and $R^8$ together with the carbon atom to which they are attached are cycloheteroalkyl or substituted cycloheteroalkyl. In still another embodiment, $R^7$ and $R^8$ together with the carbon atom to which they are attached are bridged cycloalkyl.

In one embodiment, a compound of Formula (II) is derived from a GABA analog of Formula (IV):

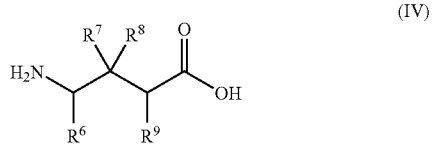

(IV)

wherein the GABA analog of Formula (IV) is selected from the group consisting of
1-Aminomethyl-1-cyclohexane acetic acid (i.e., gabapentin);
1-Aminomethyl-1-(3-methylcyclohexane) acetic acid;
1-Aminomethyl-1-(4-methylcyclohexane) acetic acid;
1-Aminomethyl-1-(4-isopropylcyclohexane) acetic acid;
1-Aminomethyl-1-(4-tert-butylcyclohexane) acetic acid;
1-Aminomethyl-1-(3,3-dimethylcyclohexane) acetic acid;
1-Aminomethyl-1-(3,3,5,5-tetramethylcyclohexane) acetic acid;
1-Aminomethyl-1-cyclopentane acetic acid;
1-Aminomethyl-1-(3-methylcyclopentane) acetic acid;
1-Aminomethyl-1-(3,4-dimethylcyclopentane) acetic acid;
7-Aminomethyl-bicyclo[2.2.1]hept-7-yl acetic acid;
9-Aminomethyl-bicyclo[3.3.1]non-9-yl acetic acid;
4-Aminomethyl-4-(tetrahydropyran-4-yl) acetic acid;
3-Aminomethyl-3-(tetrahydropyran-3-yl) acetic acid;
4-Aminomethyl-4-(tetrahydrothiopyran-4-yl) acetic acid;
3-Aminomethyl-3-(tetrahydrothiopyran-3-yl) acetic acid;
(S)-3-Aminomethyl-5-methyl-hexanoic acid (i.e., pregabalin);
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-phenyl-hexanoic acid;
3-Aminomethyl-5-phenyl-pentanoic acid;
3-Aminomethyl-4-cyclobutyl-butyric acid;
3-Aminomethyl-4-cyclopentyl-butyric acid;
3-Aminomethyl-4-cyclohexyl-butyric acid;
3-Aminomethyl-4-phenoxy-butyric acid;
3-Aminomethyl-5-phenoxy-hexanoic acid; and
3-Aminomethyl-5-benzylsulfanyl-pentanoic acid.

In one embodiment, the compound of Formula (II) is a compound of Formulae (VII) or (VIII):

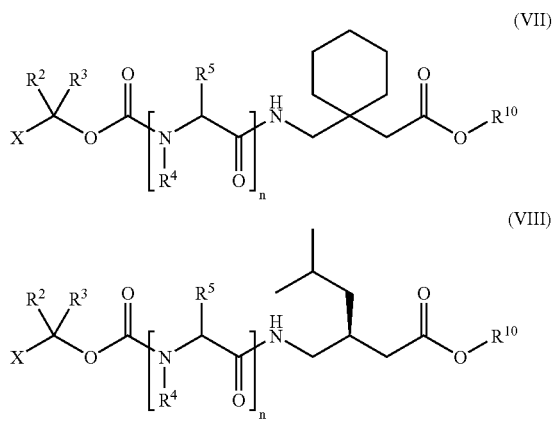

Those of skill in the art will appreciate that the following embodiments, infra, refer to compounds of Formulae (VII) and (VIII).

In one embodiment, n is 0. In another embodiment, n is 1.

In one embodiment, $R^4$ is hydrogen. In another embodiment, $R^5$ is selected from the group consisting of hydrogen, alkanyl, substituted alkanyl, aryl, substituted aryl, arylalkanyl, substituted arylalkanyl, cycloalkanyl, heteroarylalkyl and substituted heteroarylalkanyl. In another embodiment, $R^5$ is selected from the group consisting of hydrogen, methyl, isopropyl, isobutyl, sec-butyl, tert-butyl, cyclopentyl, cyclohexyl, $-CH_2OH$, $-CH(OH)CH_3$, $-CH_2CO_2H$, $-CH_2CH_2CO_2H$, $-CH_2CONH_2$, $-CH_2CH_2CONH_2$, $-CH_2CH_2SCH_3$, $CH_2SH$, $-CH_2(CH_2)_3NH_2$ and $-CH_2CH_2CH_2NHC(NH)NH_2$, phenyl, benzyl, 4-hydroxybenzyl, 4-bromobenzyl, 4-imidazolylmethyl and 3-indolylmethyl.

In still another embodiment, $R^4$ and $R^5$ together with the atoms to which they are attached form a cycloheteroalkyl or substituted cycloheteroalkyl ring. In still another embodiment, $R^4$ and $R^5$ together with the atoms to which they are attached form an azetidine, pyrrolidine or piperidine ring.

In one embodiment, X is chloro, bromo or iodo, $R^{10}$ is hydrogen, allyl, benzyl or trimethylsilyl, $R^2$ is hydrogen and $R^3$ is hydrogen. In another embodiment, X is chloro, bromo or iodo, $R^{10}$ is hydrogen, allyl, benzyl or trimethylsilyl, $R^2$ is methyl and $R^3$ is hydrogen. In still another embodiment, X is chloro, bromo or iodo, $R^{10}$ is hydrogen, allyl, benzyl or trimethylsilyl, $R^2$ is ethyl and $R^3$ is hydrogen. In still another embodiment, X is chloro, bromo or iodo, $R^{10}$ is hydrogen, allyl, benzyl or trimethylsilyl, $R^2$ is propyl and $R^3$ is hydrogen. In still another embodiment, X is chloro, bromo or iodo, $R^{10}$ is hydrogen, allyl, benzyl or trimethylsilyl, $R^2$ is isopropyl and $R^3$ is hydrogen. In still another embodiment, X is chloro, bromo or iodo, $R^{10}$ is hydrogen, allyl, benzyl or trimethylsilyl, $R^2$ is butyl and $R^3$ is hydrogen. In still another embodiment, X is chloro, bromo or iodo, $R^{10}$ is hydrogen, allyl, benzyl or trimethylsilyl, $R^2$ is isobutyl and $R^3$ is hydrogen. In still another embodiment, X is chloro, bromo or iodo, $R^{10}$ is hydrogen, allyl, benzyl or trimethylsilyl, $R^2$ is sec-butyl and $R^3$ is hydrogen. In still another embodiment, X is chloro, bromo or iodo, $R^{10}$ is hydrogen, allyl, benzyl or trimethylsilyl, $R^2$ is tert-butyl and $R^3$ is hydrogen. In still another embodiment, X is chloro, bromo or iodo, $R^{10}$ is hydrogen, allyl, benzyl or trimethylsilyl, $R^2$ is cyclohexyl and $R^3$ is hydrogen. In still another embodiment, X is chloro, bromo or iodo, $R^{10}$ is hydrogen, allyl, benzyl or trimethylsilyl, $R^2$ is phenyl and $R^3$ is hydrogen. In still another embodiment, X is chloro, bromo or iodo, $R^{10}$ is hydrogen, allyl, benzyl or trimethylsilyl, $R^2$ is methyl and $R^3$ is methyl. In still another embodiment, X is chloro, bromo or iodo, $R^{10}$ is hydrogen, allyl, benzyl or trimethylsilyl, $R^2$ is methoxycarbonyl and $R^3$ is methyl. In still another embodiment, X is chloro, bromo or iodo, $R^{10}$ is hydrogen, allyl, benzyl or trimethylsilyl, $R^2$ is ethoxycarbonyl and $R^3$ is methyl. In still another embodiment, X is chloro, bromo or iodo, $R^{10}$ is hydrogen, allyl, benzyl or trimethylsilyl, $R^2$ is isopropoxycarbonyl and $R^3$ is methyl. In still another embodiment, X is chloro, bromo or iodo, $R^{10}$ is hydrogen, allyl, benzyl or trimethylsilyl, $R^2$ is cyclohexyloxycarbonyl and $R^3$ is methyl. In still another embodiment, X is chloro, bromo or iodo, $R^{10}$ is hydrogen, allyl, benzyl or trimethylsilyl, and $R^2$ and $R^3$ together with the atom to which they are attached form a cyclohexyl ring.

In one embodiment, X is chloro, $R^{10}$ is hydrogen, allyl, benzyl or trimethylsilyl, $R^2$ is hydrogen, methyl, ethyl, n-propyl, isopropyl, n-butyl, isobutyl, sec-butyl or tert-butyl and $R^3$ is hydrogen. In another embodiment, X is chloro, $R^{10}$ is hydrogen, allyl, benzyl or trimethylsilyl, $R^2$ is methyl, n-propyl or isopropyl, and $R^3$ is hydrogen. In still another embodiment, X is chloro, $R^{10}$ is allyl, $R^2$ is methyl, and $R^3$ is hydrogen. In still another embodiment, X is chloro, $R^{10}$ is benzyl, $R^2$ is methyl, and $R^3$ is hydrogen. In still another embodiment, X is chloro, $R^{10}$ is trimethylsilyl, $R^2$ is methyl, and $R^3$ is hydrogen.

4.4 Synthesis of 1-Haloalkyl Carbamates and Conversion to 1-Acyloxy-Alkyl Carbamates The compounds and methods of the invention may be obtained and/or practiced according to the synthetic methods illustrated in Schemes 1–5. Numerous methods have been described in the art for the synthesis of GABA analogs (i.e., compounds of formula (1), infra, where n=0; see, e.g., Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Belliotti et al., International Publication No. WO 99/31074; Bryans et al., International Publication No. WO 99/31075; Bryans et al., International Publication No. WO 99/61424; Bryans et al., International Publication No. WO 00/15611; Bryans, International Publication No. WO 00/31020; and Bryans et al., International Publication No. WO 00/50027). Other methods are known in the art for synthesizing GABA analogs, which are readily accessible to the skilled artisan. Methods for synthesis of amino acid derivatives of GABA analogs (i.e., compounds of formula (1), infra, where n=1) are disclosed in Gallop et al., International Publication No. WO 02/100347).

Accordingly, starting materials useful for preparing compounds and intermediates thereof, and/or practicing methods of the invention are commercially available or can be prepared by well-known synthetic methods. Other methods for synthesis of the prodrugs described herein are either described in the art or will be readily apparent to the skilled artisan in view of the references provided above and may be used to synthesize the compounds of the invention. Accordingly, the methods presented in the Schemes herein are illustrative rather than comprehensive.

Intermediate (4) useful in the preparation of 1-haloalkyl carbamates of Formula (II) may be generated according to reactions detailed in Scheme 1.

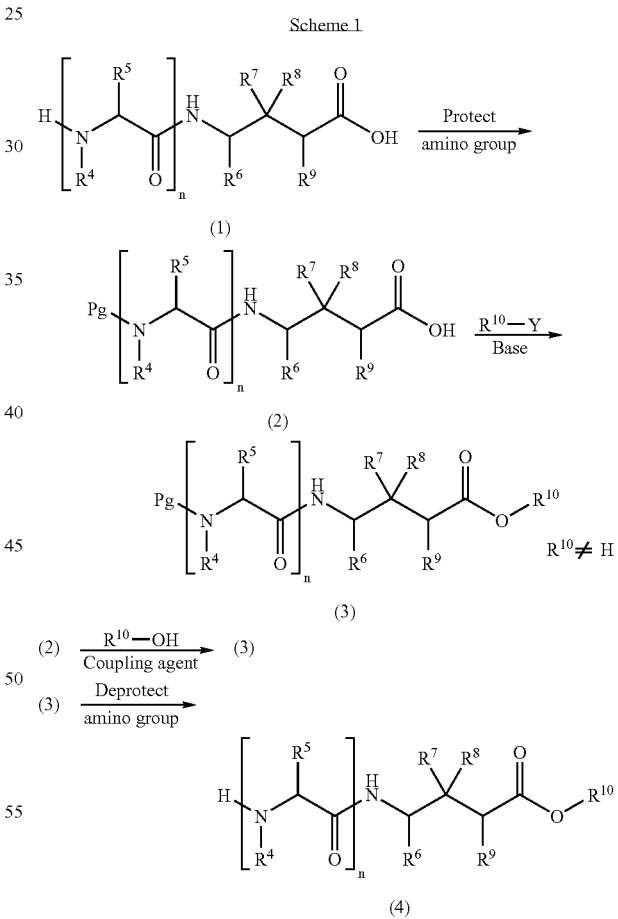

The amino group of (1) (a GABA analog when n=0, or an aminoacyl derivative of a GABA analog when n=1) is protected under standard conditions with a protecting group ("Pg") to afford compound (2). The carboxylic acid moiety in (2) is esterified to yield compound (3), either (i) via alkylation with $R^{10}$—Y, where Y is halide, $O_3SR^1$ ($R^1$ is alkyl, substituted alkyl, aryl or substituted aryl), or other suitable leaving group), or (ii) via condensation with alcohol R$^{10}$—OH under standard acylation conditions (e.g., in the presence of a coupling agent such as a carbodiimide, via an acyl halide, acid anhydride or other activated ester intermediate). Removal of the protecting group from (3) under standard deprotection conditions affords compound (4). Preferably, when n=0, the protecting group Pg is removable under acidic conditions and compound (4) is isolated as a salt, which is stabilized towards lactam formation relative to the corresponding free base form tert-Butoxycarbonyl (i.e., Boc) is one preferred protecting group, and may be removed with HCl to afford (4) as a hydrochloride salt.

In a preferred embodiment, where n is 0, the hydrochloride salt of (4) is prepared directly from (1) by treatment with an excess of thionyl chloride or hydrogen chloride gas and alcohol R$^{10}$—OH (Scheme 2). Typical ratios of (1) to thionyl chloride from between 1:1 and 1:20, and ratios of (1) to alcohol from between 1:1 and 1:20 may be used. The reaction may be performed at temperatures between −20° C. and 25° C. Under conditions where the alcohol R$^{10}$—OH is a liquid, the alcohol may be used as a solvent for the reaction. Alternatively, the reaction may be performed in the presence of a suitable solvent, such as, for example, dichloromethane, dichloroethane, chloroform, toluene, dimethylformamide, dimethylacetamide, N-methylpyrrolidinone, or pyridine. Preferred alcohols R$^{10}$—OH for this reaction are arylalkyl, substituted arylalkyl and allylic alcohols. Allyl alcohol and benzyl alcohol are particularly preferred.

Scheme 2

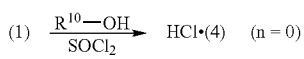

In one embodiment, a compound of formula (II) is prepared by acylation of (4) with compound (5) (see Scheme 3), where X is halide and Z is a leaving group (e.g., halide, p-nitrophenolate, imidazolyl, etc.). Preferably, X is Cl or Br and Z is Cl. More preferably, X and Z are both Cl. The acylation reaction may be performed in the presence of a base, including inorganic and organic bases (e.g., tertiary amine bases, such as triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, 1,5-diazabicyclo[4.3.0]undec-7-ene, etc.). Suitable solvents for this acylation include, but are not limited to, dichloromethane, dichloroethane, chloroform, toluene, dimethylformamide, dimethylacetamide, N-methylpyrrolidinone, dimethyl sulfoxide, pyridine, ethyl acetate, isopropyl acetate, acetonitrile, acetone, 2-butanone, methyl tert-butyl ether, or combinations thereof. Alternatively, biphasic solvent mixtures comprising water and one or more of dichloromethane, dichloroethane, chloroform, toluene, ethyl acetate, isopropyl acetate or methyl tert-butyl ether, may be utilized. Typical temperatures for performing this reaction are between −20° C. and 50° C., more preferably, between −20° C. and 25° C.

Scheme 3

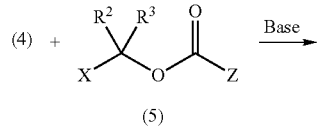

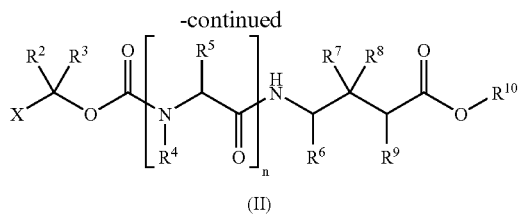

In another embodiment, a compound of formula (II), where R$^{10}$ is trialkylsilyl or aryldialkylsilyl, may be prepared directly from compound (1) by silylation (e.g., using a silyl halide or silylamide reagent) and then acylation of the resulting intermediate with compound (5) (see Scheme 4). Suitable solvents for performing this reaction include, but are not limited to, dichloromethane, dichloroethane, chloroform, toluene, pyridine, and acetonitrile. Suitable bases for performing this reaction include, but are not limited to, triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene or 1,5-diazabicyclo[4.3.0]undec-7-ene. Typical temperatures for performing this reaction are between −78° C. and 50° C., more preferably, between −20° C. and 25° C.

Scheme 4

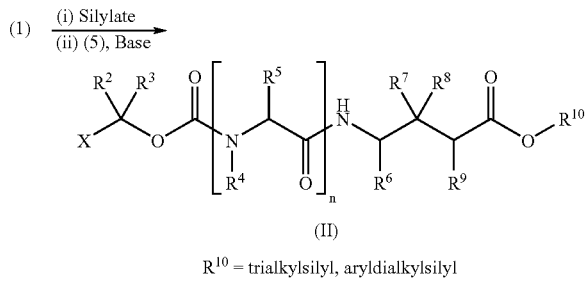

1-Acyloxyalkyl carbamates of formula (I) are prepared from compounds of formula (II) by treatment with carboxylic acids of formula (III) in the presence of an organic or inorganic base, or other metal salt, as illustrated in Scheme 5. Preferred solvents, bases and other reaction conditions have been described in detail previously (see Section 4.2 above).

Scheme 5

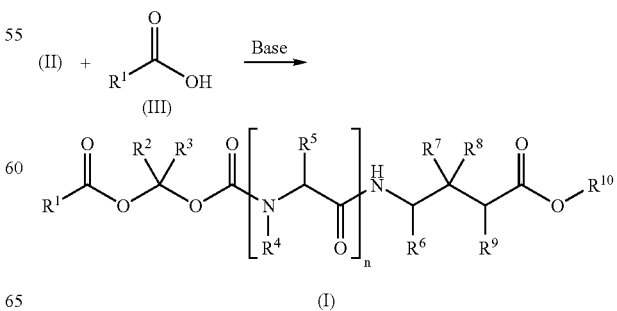

In one embodiment, $R^{10}$ is a carboxylic acid protecting group that can be removed under mild conditions to provide a compound of formula (I) where $R^{10}$ is hydrogen. Carboxylic acid protecting groups removable via mild acidic hydrolysis, fluoride ion-promoted hydrolysis, catalytic hydrogenolysis, transfer hydrogenolysis, or other transition metal-mediated deprotection reactions are preferred. In one embodiment, $R^{10}$ is trimethylsilyl, allyl or benzyl.

5. EXAMPLES

The invention is further defined by reference to the following examples, which describe in detail the preparation of 1-haloalkyl carbamates of GABA analogs and illustrate methods of synthesizing 1-(acyloxy)-alkyl carbamates of GABA analogues from 1-haloalkyl carbamates of GABA analogs. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | |
|---|---|
| Atm = | atmosphere |
| Boc = | tert-butyloxycarbonyl |
| Cbz = | carbobenzyloxy |
| DCC = | dicyclohexylcarbodiimide |
| DMAP = | 4-N,N-dimethylaminopyridine |
| DMF = | N,N-dimethylformamide |
| DMSO = | dimethylsulfoxide |
| Fmoc = | 9-fluorenylmethyloxycarbonyl |
| g = | gram |
| h = | hour |
| HPLC = | high pressure liquid chromatography |
| L = | liter |
| LC/MS = | liquid chromatography/mass spectroscopy |
| M = | molar |
| min = | minute |
| mL = | milliliter |
| mmol = | millimoles |
| NHS = | N-hydroxysuccinimide |
| THF = | tetrahydrofuran |
| TFA = | trifluoroacetic acid |
| TLC = | thin layer chromatography |
| TMS = | trimethylsilyl |
| μL = | microliter |
| μM = | micromolar |
| v/v = | volume to volume |

5.1 Example 1

Benzyl 1-Aminomethyl-1-Cyclohexane Acetate Hydrochloride (6)

A dry 500 mL, three-necked, round-bottomed flask was fitted with a magnetic stirring bar and a 60 mL pressure-equalizing addition funnel and flushed with nitrogen gas. The flask was charged with gabapentin (17.1 g, 0.1 mol) and benzyl alcohol (128 mL, 1.18 mol) and the mixture was cooled to 0° C. with an ice-water bath. Thionyl chloride (51.8 mL, 77.25 g, 0.65 mol) was added dropwise to the stirred solution over a period of 1 h. The reaction was monitored by LC/MS, with product and unreacted gabapentin hydrochloride being observed. After stirring at room temperature for 3.5 days the reaction mixture contained residual gabapentin hydrochloride (by LC/MS). Additional thionyl chloride (20 mL, 30 g, 0.25 mol) was added at 0° C., and the reaction mixture allowed to stir at room temperature for another 12 h (LC/MS shows traces of residual gabapentin hydrochloride). A final portion of thionyl chloride (10 mL, 15 g, 0.12 mol) was added at 0° C. and the reaction mixture allowed to stir at room temperature for 4 h (LC/MS showed no remaining gabapentin hydrochloride). The reaction mixture was then diluted with ethyl ether (200 mL) and cooled to 0° C. while stirring. White crystalline solid formed, which was collected by filtration. The crude compound was recrystallized from a mixture of ethanol and ethyl ether (50 mL: 150 mL). Finally the white crystals were washed with 250 mL of ethyl acetate to give product (6) as a white solid (27 g, 91% yield). $^1$H NMR (CDCl$_3$, 400 MHz.): δ 1.43–1.52 (m, 10H), 2.64 (s, 2H), 3.08 (d, 2H), 6.04 (br. s, 11H), 7.25–7.33 (m, 5H), 8.44 (br. s, 3H). MS (ESI) m/z 262.26 (M+H$^+$).

5.2 Example 2

1-[(tert-Butoxycarbonyl)aminomethyl]-1-Cyclohexane Acetic Acid (7)

Gabapentin, (700 g, 4.09 mol) was slurried in water (2.7 L) with potassium carbonate (1.2 kg, 8.58 mol) and mechanically stirred under a nitrogen atmosphere. Di-tert-butyl dicarbonate (875 g, 4.00 mol) was dissolved in dioxane (4 L) and was added in large aliquots while maintaining the pH at 8–10, and if needed, adjusting the pH using additional potassium carbonate. The reaction was monitored by $^1$H-NMR, noting the disappearance of the singlet resonance at 1.22 ppm for di-tert-butyl dicarbonate. After stirring overnight at ambient temperature the dioxane was removed in vacuo and the pH of the aqueous phase adjusted to between 3 and 4 using 10% sulfuric acid. The aqueous mixture was extracted with ethyl acetate, the organic layer was washed with brine, dried over sodium sulfate and concentrated in vacuo to afford compound (7) as a white powder (893 g, 80% yield). $^1$H NMR (CDCl$_3$), 400 MHz): δ 1.24–1.50 (m, 110H), 2.30 (s, 2H), 3.15 (d, 2H), 5.02 (t, 11H). MS (ESI) m/z 294.18 (M+Na$^+$). Melting point: 125–130° C.

5.3 Example 3

Benzyl 1-[(tert-Butoxycarbonyl)aminomethyl]-1-Cyclohexane Acetate (8)

In a 12 L, multi-neck, round bottom flask with a bottom valve, mechanical stirrer and nitrogen blanket, (7) (1098 g, 4.05 mol) and potassium carbonate (838 g, 6.075 mol) were added to N-methylpyrrolidinone (2 L) at room temperature. Benzyl bromide (457 mL, 3.84 mol) was added over one hour. The strongly exothermic reaction was maintained below 40° C., and the resulting white suspension was stirred until judged complete by NMR, about 2 hours.

Ice water (6 L) was carefully added to quench the reaction. Dichloromethane (3 L) was added, the organic phase separated and further extracted with water (2×2 L), 10% potassium carbonate (2×2 L), brine (2 L), then dried over sodium sulfate and concentrated in vacuo. The crude product (8) (~1380 g, 94% yield) was carried to the next reaction without further purification. $^1$H NMR (CDCl$_3$, 400 MHz): 1.33–1.53 (m, 10H), 2.32 (s, 2H), 3.11 (d, 2H), 5.01 (br. t, 1H), 5.09 (s, 2H), 7.31–7.35 (m, 5H). MS (ESI) m/z 442.39 (M+Na$^+$).

5.4 Example 4

Benzyl 1-Aminomethyl-1-Cyclohexane Acetate Hydrochloride (6)

Compound (8) from Example 3 above was added slowly with stirring and cooling to a 5 L, 3-neck, round bottom flask containing 4N HCl in dioxane (2.5 L) over about a one hour period, the reaction mixture being maintained between 30 and 35° C. to keep the product from precipitating. The clear solution was divided into four aliquots, to each of which was added methyl-t-butyl ether (500 mL) to initiate crystallization of the product. Each batch fully solidified within 10 min. The solids were filtered, washed twice with ethyl acetate, then dried in a vacuum oven at 35° C. for 16 h to afford the product (6) as a white solid (936 g, 79% yield from (7)). $^1$H NMR (CDCl$_3$, 400 MHz.): δ 1.43–1.52 (m, 10H), 2.64 (s, 2H), 3.08 (d, 2H), 6.04 (br. s, 1H), 7.25–7.33 (m, 5H), 8.44 (br. s, 3H). MS (ESI) m/z 262.26 (M+H$^+$).

5.5 Example 5

Benzyl 1-{[(α-Chloroethoxy)carbonyl]aminomethyl}-1-Cyclohexane Acetate (9)

In a 5-liter, 3-neck, round bottom flask, stirred mechanically and under nitrogen, was added dichloromethane (1.5 L), compound (6) (1.85 mol) and l-chloroethyl chloroformate (258 g, 1.81 mol). The resulting solution was cooled to 15° C. and N-methylmorpholine (396 mL, 3.60 mol) was added slowly, with cooling, over a one hour period. The resulting turbid solution was stirred for 30 min, after which $^1$H-NMR analysis showed the reaction to be complete. The reaction mixture was washed with water (2×2 L) and brine (1 L) and dried over sodium sulfate. Evaporation of the solvent afforded the title compound (9) as an orange oil (670 g, 98% yield). $^1$HNMR (CDCl$_3$, 400 MHz): 1.33–1.53 (m, 10H), 1.75 (d, 3H), 2.33 (s, 2H), 3.18 (d, 2H), 5.09 (s, 2H), 5.58 (t, 1H), 6.53 (q, 1H), 7.29–7.33 (m, 5H).

5.6 Example 6

Benzyl 1-{[(α-Isobutanoyloxyethoxy)carbonyl]aminomethyl}-1-Cyclohexane Acetate (10)

To a 110-L reactor equipped with a mechanical stirrer, cooling jackets and under nitrogen, was added isobutyric acid (1.35 L, 14.6 mol) via an addition funnel, followed by N-methylmorpholine (1.6 L, 14.6 mol). The resulting solution was cooled to 16° C. and a solution containing compound (9) (1237 g crude, 2.93 mol) dissolved in isobutyric acid (1.35 L 14.6 mol) was slowly added with stirring. After the addition was complete the resulting turbid solution was stirred for a total of 33 h, after which time $^1$H-NMR indicated less than 2% of starting material (9) remained. The crude reaction mixture was split in two equal batches, each of which was diluted with diethyl ether (6 L), washed with water (6×2L) in a centrifugal extractor to remove excess isobutyric acid, followed by washing with 10% potassium bicarbonate (4×2 L) and brine (2×2 L) before drying over anhydrous sodium sulfate. The combined organic extracts were concentrated to provide a dark orange oil (916 g). The crude oil (400 g) was loaded onto an 800 g Biotage™ silica gel chromatography column and eluted with 5% ethyl acetate in hexane (6 L), then with 7% ethyl acetate in hexane (12 L). The desired product elutes in the 7% fractions. The chromatographic purification was repeated with the remaining crude product to afford compound (10) as a thick colorless oil (822 g). $^1$H NMR (CDCl$_3$, 400 MHz): δ 1.5 (d, 6H), 1.24–1.53 (m, 13H), 1.45 (d, 3H),2.33 (s, 2H), 2.48–2.55 (m, 1H), 3.16 (d, 2H), 5.09 (s, 2H), 5.35 (t, 1H), 6.77 (q, 1H), 7.29–7.36 (m, 5H). MS (ESI) m/z 442.48 (M+Na$^+$).

5.7 Example 7

1-{[(α-Isobutanoyloxyethoxy)carbonyl]aminomethyl}-1-Cyclohexane Acetic Acid (11)

Compound (10) (113 g) was dissolved in ethyl acetate (700 mL) and 10 g of 10% Pd-C was added. The reaction mixture was subjected to 50 psi of hydrogen gas in a Parr reactor for 40 min. Filtration through a sintered glass funnel and a hydrophobic membrane filtration cartridge (Millipore Opticap) removed the catalyst. The supernatant was concentrated to afford the product (11) as a white, crystalline solid (78 g, quantitative yield). Crystals formed in the freezer, then at room temperature over several days. $^1$H NMR (CDCl$_3$, 400 MHz): 1.15 (d, 6H), 1.40–1.55 (m, 10H), 1.45 (d, 3H), 2.32 (s, 2H), 2.49–2.56 (m, 1H), 3.23 (d, 2H), 5.41 (t, 1H), 6.75 (q, 1H). MS(ESI) m/z 330.29 (M+H$^+$).

A portion of the product (25 g) was recrystallized by dissolution in 1:10 ethyl acetate:heptane (125 mL) at 60° C., then slow cooling to 4° C. The white crystalline product (21 g) was isolated by filtration. Melting point: 63–64° C. Differential scanning calorimetry endotherm: 63° C.

5.8 Example 8

Sodium 1-{[(α-Isobutanoyloxyethoxy)carbonyl]-aminomethyl}-1-Cyclohexane Acetate (12)

Compound (11) (540 g, 1.64 mol) was dissolved in acetone (850 mL) and water (500 mL) in a 4 L beaker, equipped with overhead stirring, pH meter and addition funnel. Aqueous sodium carbonate (1.0 M) was added slowly in 50 mL aliquots. After addition of 0.49 eq. base (803 mL of sodium carbonate solution) the pH was 7.3. Acetone was removed in vacuo at 25° C. and the pH re-checked to be ~6.5. The remaining aqueous solution was divided into three 3-L flasks, shell frozen and lyophilized for two days. The resulting sodium salt (12) was scraped from the flasks as a hygroscopic solid and transferred quickly into bottles, which were immediately capped and transferred into a drying chamber at 14% relative humidity (RH). The remaining oily product in the flasks was dissolved in diethyl ether and concentrated in vacuo at 25° C., then dried under high vacuum until a dry foam was produced.

5.9 Example 9

Allyl 1-Aminomethyl-1-Cyclohexane Acetate Hydrochloride (13)

A dry 500 mL, three-neck, round-bottomed flask was fitted with a magnetic stirring bar and a 100 mL pressure-equalizing addition funnel and flushed with nitrogen gas. The flask was charged with gabapentin (17.1 g, 0.1 mol) and allyl alcohol (100 mL, 1.46 mol) and the entire mixture was cooled to 0° C. in an ice-water bath. Thionyl chloride (22.5 mL, 36 g, 0.3 mol) was added drop-wise over a period of 30 min to the stirred solution, and the reaction mixture allowed to stir for 16 h at room temperature. The mixture was then diluted with diethyl ether (200 mL) and cooled to 0° C.

while stirring. After several minutes white crystals formed, and were collected by filtration. The crude compound was recrystallized from a mixture of ethanol and diethyl ether (50 mL: 150 mL) to give the product (13) as a white solid (22 g, 88% yield), m.p: 138–142° C. $^1$H NMR (CD$_3$OD, 400 MHz): δ 1.36–1.54 (m, 10H), 2.57 (s, 2H), 3.05 (s, 2H), 4.61 (d, 2H), 5.22 (dd, 1H), 5.33 (dd, 1H), 5.90–6.00 (m, 1H). MS (ESI) m/z 212.0 (M+H$^+$).

5.10 Example 10

Allyl 1-{[(α-Chloroethoxy)carbonyl]aminomethyl}-1-Cyclohexane Acetate (14)

To a solution of compound (13) (30 g, 0.121 mol) in dichloromethane (100 mL) was slowly added 1-chloroethyl chloroformate (13 mL, 16.9 g, 0.119 mol). The reaction mixture was cooled to 0° C. and N-methylmorpholine (26.39 mL, 24.28 g, 0.24 mol) was slowly added over a period of 1 h while maintaining a temperature of less than 10° C. The resulting turbid solution was stirred for 30 min, and the reaction mixture was then diluted with diethyl ether (250 mL), washed with water (100 mL) and brine (100 mL). The organic phase was dried over anhydrous sodium sulfate and concentrated to give the desired product (14) as light yellow viscous liquid (38 g, 99% yield). $^1$H NMR (CDCl$_3$, 400 MHz): δ 1.35–1.58 (m, 10H), 1.78 (d, 3H), 2.32 (s, 2H), 3.22 (d, 2H), 4.57 (d, 2H), 5.25 (dd, 1H), 5.32 (dd, 1H), 5.52 (br. s, 1H), 5.90–5.94 (m, 1H), 6.54 (q, 1H).

5.11 Example 11

Allyl 1-{[(α-Isobutanoyloxyethoxy)carbonyl]aminomethyl}-1-Cyclohexane Acetate (15)

A solution of compound (14) (38 g, 0.12 mol) in isobutyric acid (55 mL, 52.5 g, 0.6 mol) was added to a mixture of isobutyric acid (55 mL, 52.5 g, 0.6 mol) in N-methylmorpholine (65 mL, 60 g, 0.59 mol) at 0° C. over a period of 30 min. The resulting turbid solution was stirred for 16 h at room temperature. The reaction mixture was diluted with diethyl ether (500 mL) and washed with water (3×200 mL) followed by 10% potassium bicarbonate (4×200 mL) and brine (200 mL). The organic phase was dried over anhydrous sodium sulfate and concentrated to yield a viscous liquid. This crude product was purified by column chromatography on silica gel, eluting with 7.5% ethyl acetate:hexane to give the desired compound (15) as a clear, viscous liquid (37 g, 84% yield). $^1$H NMR (CDCl$_3$, 400 MHz): δ 1.15 (d, 6H), 1.35–1.58 (m, 10H), 2.31 (s, 2H), 2.51 (m, 1H), 3.19 (d, 2H), 4.56 (d, 2H), 5.24 (dd, 1H), 5.32 (dd, 1H), 5.35 (br. s, 1H), 5.84–5.94 (m, 1H), 6.78 (q, 1H). MS (ESI) m/z 392.24 (M+H$^+$).

5.12 Example 12

1-{[(α-Isobutanoyloxyethoxy)carbonyl]aminomethyl}-1-Cyclohexane Acetic Acid (11)

Method A: To a stirred suspension of ammonium formate (3.4 g, 54 mmol) in ethanol (34 mL), was added compound (15) (10 g, 27 mmol) together with 10% Pd/C (1 g) under a nitrogen atmosphere. After one hour, the reaction mixture was filtered and the catalyst washed with ethanol (2×10 mL). The filtrates were combined and evaporated. The crude product was dissolved in diethyl ether (150 mL) and the organic phase was washed with 2N HCl (100 mL), water (100 mL) and brine (100 mL). The ether layer was dried over anhydrous sodium sulfate and concentrated to give a viscous liquid that crystallized upon standing. The product was recrystallized using 1:10 ethyl acetate:heptane (100 mL) to give the product (11) as a white, crystalline solid (7.9 g, 88%), m.p 63–64° C.

Method B: To a stirred solution of compound (15) (1 g, 2.7 mmol) in acetonitrile (10 mL) under nitrogen was added (10 mg, 0.008 mmol) of tetrakis(triphenylphosphine) palladium (0) followed by morpholine (0.28 mL, 0.28 g, 3.2 mmol). After one hour, the solvent was removed in vacuo. The resulting oil was dissolved in diethyl ether (50 mL) and the organic phase was washed with 2N HCl (20 mL), water (20 mL) and brine (20 mL). The ether layer was dried over anhydrous sodium sulfate and concentrated to give an oil, which was purified by column chromatography on silica gel, eluting with 30% ethyl acetate:hexane. The desired product (11) was isolated as a white crystalline solid (0.75 g, 84% yield), m.p 63–64° C.

Method C: To a stirred solution of compound (15) (1 g, 2.7 mmol) in dioxane (9 mL) was added ammonium formate (341 mg, 2.7 mmol) and palladium (II) acetate (12 mg) under a nitrogen atmosphere. The reaction mixture was heated to reflux for one hour and then concentrated in vacuo. The resulting oily residue was taken up in diethyl ether (50 mL), washed with 2N HCl (20 mL), water (20 mL) and brine (20 mL). The organic phase was dried over anhydrous sodium sulfate and evaporated to dryness. The crude compound was purified by column chromatography on silica gel, eluting with 30% ethyl acetate:hexane to give the desired product (11) as a colorless oil, which solidified on further standing at room temperature for 12 h (0.70 g, 78% yield), m.p. 62–64° C.

5.13 Example 13

1-{[(α-Chloroethoxy)carbonyl]aminomethyl}-1-Cyclohexane Acetic Acid (16) via Trimethylsilyl 1-{[(α-Chloroethoxy)carbonyl]aminomethyl}-1-Cyclohexane Acetate (17)

In a 5-liter, 3-neck, round bottom flask containing dichloromethane (1.6 L) was added gabapentin (120.4 g, 0.704 mol) followed by triethylamine (294 mL, 2.11 mol). Chlorotrimethylsilane (178 mL, 1.40 mol) was slowly added while maintaining the reaction temperature below 15° C. and the resulting suspension was stirred for 30 min. 1-Chloroethyl chloroformate (100 g, 0.704 mol) was then added slowly while maintaining the temperature below 15° C. After the addition was complete, additional triethylamine (88 mL, 0.63 mol) was added and the resulting suspension was stirred at room temperature for 30 min. The resulting silyl ester (17) was converted via acidic work-up to the corresponding acid (16) by washing the reaction mixture with water (2×1 L), followed by 1N HCl (2×2 L) then brine (2×500 mL). After drying over anhydrous sodium sulfate and removal of the solvent in vacuo, the crude product (190 g) was obtained as an orange oil and used in Example 14 without further purification. $^1$H NMR (CDCl$_3$, 400 MHz): δ 1.41–1.57 (m, 10H), 1.78 (d, 3H), 2.33 (s, 2H), 3.27 (d, 2H), 5.42 (br. s, 1H), 6.55 (q, 1H).

5.14 Example 14

1-{[(α-Isobutanoyloxyethoxy)carbonyl]aminomethyl}-1-Cyclohexane Acetic Acid (11)

To a 3-liter, 3-neck, round bottom flask was added isobutyric acid (254 g, 2.9 mol) followed by triethylamine (395 ml, 2.84 mol). The reaction mixture was cooled to room temperature and a solution of crude (16) from the above example (190 g, 0.69 mol) in dichloromethane (80 mL) was added in a controlled fashion to maintain the temperature below 30° C. The resulting pale yellow solution was stirred overnight. The reaction mixture was then diluted with one volume of dichloromethane and washed with water (6×500 mL), aqueous potassium bicarbonate (3×500 mL), and brine (2×500 mL). After drying over anhydrous sodium sulfate, removal of the solvent in vacuo afforded the crude product as a dark red oil (87 g). A portion (35 g) of this product was loaded onto an 800 g Biotage™ normal phase silica gel flash column and eluted with 40% diethyl ether in hexane (6 L), which after removal of the solvent in vacuo afforded product (11) as a colorless oil. This was repeated with a second 35 g portion of crude product yielding a further 13.5 g of (11). A sample of the product (25 g) was recrystallized by dissolution in heptane (325 mL) at 70° C., then slow cooling to room temperature. The white crystalline product (11) (23 g) was isolated by filtration. Melting point: 63–64° C.

5.15 Example 15

1-{[(α-Chlorobutoxy)carbonyl]aminomethyl}-1-Cyclohexane Acetic Acid (18) via Trimethylsilyl 1-{[(α-Chlorobutoxy)carbonyl]aminomethyl}-1-Cyclohexane Acetate (19)

In a 5-liter, 3-neck, round bottom flask containing dichloromethane (1.6 L) was added gabapentin (113.5 g, 0.66 mol) followed by diisopropylethylamine (193.5 mL, 1.1 mol). Chlorotrimethylsilane (88.1 mL, 0.69 mol) was slowly added while maintaining the reaction temperature below 15° C. and the resulting suspension was stirred for 30 min. 1-Chlorobutyl chloroformate (108 g, 0.63 mol) was then added slowly while maintaining the temperature below 15° C., and the resulting suspension was stirred at room temperature for 30 min. The resulting silyl ester (19) was converted via acidic work-up to the corresponding acid (18) by washing the reaction mixture with water (2×1 L), followed by 1N HCl (2×1 L) then brine (2×500 mL). After drying over anhydrous sodium sulfate and removal of the solvent in vacuo, the crude product (116 g, 60% yield) was obtained as an off-white solid and used in Example 16 without further purification. $^1$H NMR (CDCl$_3$, 400 MHz): δ 0.93 (t, 3H), 1.28–1.62 (m, 12H), 1.92–2.06 (m, 2H), 2.35 (s, 2H), 3.28 (d, 2H), 5.44 (t, 1H), 6.45 (t, 1H).

5.16 Example 16

1-{[(α-Propanoyloxybutoxy)carbonyl]aminomethyl}-1-Cyclohexane Acetic Acid (20)

To a 1-L, 3-neck, round bottom flask was added propionic acid (200 mL, 2.68 mol) followed by triethylamine (50.7 mL, 0.36 mol). The reaction mixture was cooled to room temperature and a solution of crude (18) from the above example (101 g, 0.33 mol) in dichloromethane (80 mL) was added in a controlled fashion to maintain the temperature below 30° C. The resulting pale yellow solution was stirred overnight. The reaction mixture was then diluted with one volume of dichloromethane and washed with water (6×250 mL), aqueous potassium bicarbonate (3×250 mL), and brine (2×250 mL). After drying over anhydrous sodium sulfate, removal of the solvent in vacuo afforded the crude product as a dark red oil (100 g). A portion (40 g) of this product was loaded onto an 800 g Biotage™ normal phase silica gel flash column and eluted with 20% diethyl ether in hexane (6 L), which after removal of the solvent in vacuo afforded product (20) as a colorless oil (15 g). $^1$H NMR (CDCl$_3$, 400 MHz): 0.95 (t, 3H), 1.13 (t, 3H), 1.32–1.60 (m, 12H), 1.70–1.78 (m, 2H), 2.28–2.38 (m, 4H), 3.24 (d, 2H), 5.24 (t, 1H), 6.71 (t, 11H). MS(ESI) m/z 343.44 (M+H$^+$).

5.17 Example 17

1-{[(α-Chloroisobutoxy)carbonyl]aminomethyl}-1-Cyclohexane Acetic Acid (21) via Trimethylsilyl 1-{[(α-Chloroisobutoxy)-carbonyl]aminomethyl}-1-Cyclohexane Acetate (22)

To a mixture containing gabapentin (1.71 g, 10 mmol) and triethylamine (3.06 mL, 22 mmol) in dichloromethane (150 mL) was added chlorotrimethylsilane (1.4 mL, 11 mmol) and the resulting mixture was stirred until clear (about 20 min). A solution containing 1-chloro-2-methylpropylchloroformate (1.27 mL, 11 mmol) in dichloromethane (10 mL) was then added at 0° C. and stirred at room temperature for 60 min. The resulting silyl ester (22) was converted via acidic work-up to the corresponding acid (21) by washing the reaction mixture with 10% citric acid (30 mL) and the organic layer separated. The aqueous layer was further extracted with ether (3×20 mL) and the combined organic phases were dried over MgSO$_4$ and then concentrated in vacuo. Chromatography of the residue on silica gel, eluting with hexane:ethyl acetate (1:4) gave the title compound (21) (2.37 g, 77%). $^1$H NMR (CDCl$_3$, 400 MHz): δ 1.04 (d, J=6.4 Hz, 3H), 1.06 (d, J=6.4 Hz, 3H), 1.36–1.53 (m, 10 H), 2.15 (m, 1H), 2.34 (s, 2H), 3.24 (m, 2H), 5.39 (t, 1H), 6.32 (d, J=5.6 Hz), 1H). MS (ESI) m/z 306.34 (M+H$^+$).

5.18 Example 18

1-{[(α-Nicotinoyloxyisobutoxy)carbonyl]aminomethyl}-1-Cyclohexane Acetic Acid (23)

A mixture of (21) (268 mg, 0.88 mmol), 1,8-diazabicyclo[5.4.0]undec-7-ene (DBU) (158 μL, 1.01 mmol), and nicotinic acid (637 mg, 5.2 mmol) in acetone was stirred at room temperature for 48 h. After filtration, the filtrate was concentrated in vacuo and the resulting residue was purified by reverse phase preparative HPLC to afford the title compound (23) (50 mg, 14%). $^1$H NMR (CD$_3$OD, 400 MHz): δ 1.07 (d, 3H), 1.09 (d, 3H), 1.32–1.58 (m, 10H), 2.19 (m, 1H), 2.26 (s, 2H), 3.23 (m, 2H), 6.78 (d, 1H), 7.58 (m, 1H), 8.39 (d, 1H), 8.76 (d, 1H), 9.10 (s, 1H). MS (ESI) m/z 393.42 (M+H$^+$).

5.19 Example 19

Benzyl 1-{[(α-Chloroisobutoxy)carbonyl]aminomethyl}-1-Cyclohexane Acetate (24)

To a solution of (21) (1.02 g, 3.34 mmol) in dichloromethane was added 1,3-dicyclohexylcarbodiimide (758 mg, 3.67 mmol). After stirring at room temperature for 30 min, benzyl alcohol (380 μL, 3.67 mmol) and 4-(dimethylamino)pyridine (catalytic amount) were added. The resulting mixture was stirred at room temperature of 16 h. After filtration, the filtrate was washed with 10% citric acid, dried over Na$_2$SO$_4$, and concentrated. Chromatography of the residue on silica gel, eluting with 10% ethyl acetate/hexane, gave the title compound (24) (820 mg, 62%). $^1$H NMR (CDCl$_3$, 400 MHz): δ 1.03 (d, 3H), 1.05 (d, 3H), 1.36–1.53

(m, 10H), 2.13 (m, 1H), 2.35 (s, 2H), 3.22 (m, 2H), 5.11 (s, 2H), 5.49 (t, 1H), 6.32 (d, 1H), 7.34 (m, 5H). MS (ESI) m/z 396.24 (M+H$^+$).

5.20 Example 20

Cesium 2,2-Diethoxypropionate (25)

To a stirred solution of pyruvic acid (14 mL, 0.2 mol) and triethylorthoformate (80 mL) at 10° C. was added concentrated sulfuric acid (1 mL). The resulting mixture was stirred at 5–10° C. for 1 h and then diluted with dichloromethane (200 mL). The organic solution was washed successively with water (3×80 mL) and saturated sodium chloride solution (80 mL) and then dried over anhydrous sodium sulfate. The mixture was filtered and then concentrated to give a quantitative yield of 2,2-diethoxypropionic acid as an oil. $^1$H NMR (CDCl$_3$, 400 MHz): δ 1.30 (t, 6H), 1.61 (s, 3H), 3.57 (q, 4H), 8.62 (s, 1H). The acid form was quantitatively converted to its cesium salt (25) by dissolving the acid in water (25 mL) followed by treatment with an equimolar quantity of cesium carbonate, and then lyophilization. $^1$H NMR (D$_2$O, 400 MHz): δ 0.98 (t, 6H), 1.28 (s, 3H), 3.22 (q, 2H), 3.47 (q, 2H).

5.21 Example 21

Benzyl 1-{[(α-2,2-Diethoxypropanoyloxyisobutoxy) carbonyl]-aminomethyl}-1-Cyclohexane Acetate (26)

A mixture of (24) (200 mg, 0.51 mmol) and sodium iodide (114 mg, 0.76 mmol) in acetone was stirred at room temperature for 1 h. Cesium 2,2-diethoxypropionate (25) (300 mg, 1.02 mmol) and DMF (20 mL) were added and the resulting mixture was stirred at 40° C. for 18 h. After filtration, the filtrate was concentrated and the resulting residue was purified by silica gel flash column chromatography, eluting with 10% ethyl acetate/hexane to afford the title compound (26) (100 mg, 37% yield). MS (ESI) m/z 522.34 (M+H$^+$).

5.22 Example 22

1-{[(α-2,2-Diethoxypropanoyloxyisobutoxy)carbonyl]-aminomethyl}-1-Cyclohexane Acetic Acid (27)

A mixture of (26) (200 mg, 0.38 mmol) and 5% Pd—C (catalytic amount) was stirred under hydrogen at room temperature for 16 h. After filtration, the filtrate was concentrated and the resulting residue was purified by reverse phase preparative HPLC to afford the title compound (27) (98 mg, 60% yield). $^1$H NMR (CDCl$_3$, 400 MHz): δ 0.97 (d, J 6H), 1.19 (t, 3H), 1.21 (t, 3H), 1.32–1.58 (m, 10H), 1.51 (s, 3H), 2.06 (m, 1H), 2.30 (s, 2H), 3.23 (m, 2H), 3.46 (m, 2H), 3.56 (m, 2H), 5.30 (t, 1H), 6.59 (d, 1H). MS (ESI) m/z 432.24 (M+H$^+$).

5.23 Example 23

1-{[(α-(2-Amino-2-methylpropanoyl)oxyisobutoxy)-carbonyl]aminomethyl}-1-Cy Clohexane Acetic Acid (28)

Following the procedures of Examples 20–22, and substituting 2-amino-2-methylpropionic acid for 2,2-diethoxypropionic acid, provided the title compound (28). $^1$H NMR (CDCl$_3$, 400 MHz): δ 0.97 (d, 6H), 1.44 (s, 3H), 1.45 (s 3H), 1.32–1.58 (m, 10H,), 2.05 (m, 1H), 2.30 (s, 2H), 3.23 (m, 2H), 5.50 (t, 1H), 6.58 (d, 1H). MS (ESI) m/z 373.48 (M+H$^+$).

5.24 Example 24

Methyl 1-{[(α-Chloroisobutoxy)carbonyl]aminomethyl}-1-Cyclohexane Acetate (29)

A mixture of (21) (1.0 g, 3.3 mmol), benzene (90 mL), and methanol (10 mL) was cooled to 0° C. Trimethylsilyldiazomethane was added slowly at 0° C. until the yellow color persisted. The mixture was stirred at 0° C. for 30 min until the reaction was complete (monitored by TLC). After removing the solvent under reduced pressure, chromatography of the resulting residue on silica gel, eluting with 10% ethyl acetate/hexane gave the title compound (29) (760 mg, 72%). MS (ESI) m/z 320.24 (M+H$^+$).

5.25 Example 25

Methyl 1-{[(α-Isobutanoyloxyisobutoxy)carbonyl]-aminomethyl}-1-Cyclohexane Acetate (30)

A mixture of (29) (760 mg, 2.38 mmol), silver carbonate (394 mg, 1.4 mmol), and isobutyric acid (442 μL, 4.76 mmol) in chloroform was stirred at room temperature for 24 h. Another batch of silver carbonate (394 mg, 1.4 mmol) and isobutyric acid (442 μL, 4.76 mmol) was added, and the resulting mixture was stirred for another 24 h. After filtration, the filtrate was concentrated and the resulting residue purified by silica gel flash column chromatography, eluting with 10% ethyl acetate/hexane, to afford the title compound (30) (560 mg, 63%). $^1$H NMR (CDCl$_3$, 400 MHz): δ 0.94 (d, 3H), 0.96 (d, 3H), 1.15 (d, 3H), 1.17 (d, 3H), 1.32–1.58 (m, 10H), 2.01 (m, 1H), 2.19 (s, 2H), 2.55 (m, 1H), 3.18 (m, 2H), 3.67 (s, 3H), 5.33 (t, 1H), 6.56 (d, 1H). MS (ESI) m/z 372.38 (M+H$^+$).

5.26 Example 26

3-{[(α-Chloroethoxy)carbonyl]aminomethyl}-5-Methyl-Hexanoic Acid (31) via Trimethylsilyl 3-{[(α-Chloroethoxy)carbonyl]aminomethyl}-5-Methyl-Hexanoate (32)

To a stirred suspension of pregabalin (270 mg, 1.38 mmol) in dichloromethane (5 mL) at −20° C. was added triethylamine (0.58 mL, 4.14 mmol) and a 1 M solution of chlorotrimethylsilane in dichloromethane (2.76 mL, 2.76 mmol). The resulting reaction mixture was allowed to warm to 0° C., and stirred for 20 min. The solution was then cooled again to −20° C. and 1-chloroethyl chloroformate (0.151 mL, 1.38 mmol) added. The reaction mixture was stirred at 0° C. for an additional 30 min. The resulting silyl ester (32) was converted via acidic work-up to the corresponding acid (31) by quenching the reaction mixture with citric acid, diluting with dichloromethane, washing with water and brine, then drying over anhydrous Na$_2$SO$_4$. Filtration and evaporation afforded the title compound (31) (300 mg), which was used in the following example without further purification.

5.27 Example 27

3-{[(α-Isobutanoyloxyethoxy)carbonyl]aminomethyl}-5-Methyl-Hexanoic Acid (33)

A solution of the above crude product (31) (320 mg) in dichloromethane (2 mL) was added to a mixture of isobutyric acid (1 mL) and N-methylmorpholine (0.5 mL) at 0° C. The resulting mixture was stirred for 24 h at ambient temperature. The mixture was then diluted with dichloromethane, washed twice with water and brine, and dried over anhydrous $Na_2SO_4$. After filtration and removal of the solvent in vacuo, the crude product was purified by reverse phase preparative HPLC to afford the product (33) (70 mg, 16%) as a mixture of two diastereoisomers. $^1$H-NMR ($CDCl_3$, 400 MHz): δ 0.89 (m, 6H), 1.16 (m, 8H), 1.46 (d, 3H), 1.66 (m, 1H), 2.11–2.36 (m, 3H), 2.52 (m, 1H), 3.11 (m, 1H), 3.27 (m, 1H), 5.08 (t, 1H), 6.77 (m, 1H). MS (ESI) m/z 316.20 (M−H⁻).

5.28 Example 28

3-{[(α-Chloroisobutoxy)carbonyl]aminomethyl}-5-Methyl-Hexanoic Acid (34) via Trimethylsilyl 3-{[(α-Chloroisobutoxy)carbonyl]-aminomethyl}-5-Methyl-Hexanoate (35)

To a stirred suspension of pregabalin (270 mg, 1.38 mmol) in dichloromethane (5 mL) at −20° C. was added triethylamine (0.58 mL, 4.14 mmol) and a 1 M solution of chlorotrimethylsilane in dichloromethane (2.76 mL, 2.76 mmol). The resulting reaction mixture was allowed to warm to 0° C., and stirred for 20 min. The solution was then cooled again to −20° C. and 1-chloro-2-methylpropyl chloroformate (0.201 mL, 1.38 mmol) added. The reaction mixture was stirred at 0° C. for an additional 30 min. The resulting silyl ester (35) was converted via acidic work-up to the corresponding acid (34) by quenching the reaction mixture with citric acid, diluting with dichloromethane, washing with water and brine, then drying over anhydrous $Na_2SO_4$. Filtration and evaporation afforded the title compound (34) (300 mg), which was used in the following example without further purification.

5.29 Example 29

3-{[(α-Isobutanoyloxyisobutoxy)carbonyl]aminomethyl}-5-Methyl-Hexanoic Acid (36)

A solution of the above crude product (34) (300 mg) in dichloromethane (2 mL) was added to a mixture of isobutyric acid (1 mL) and N-methylmorpholine (0.5 mL) at 0° C. The resulting mixture was stirred for 24 h at ambient temperature. The mixture was then diluted with dichloromethane, washed twice with water and brine, and dried over anhydrous $Na_2SO_4$. After filtration and removal of the solvent in vacuo, the crude product was purified by reverse phase preparative HPLC to afford the product (36) (27 mg, 6%) as a mixture of two diastereoisomers. $^1$H-NMR ($CDCl_3$, 400 MHz): δ 0.88 (m, 6H), 0.95 (d, 6H), 1.17 (m, 8H), 1.64 (m, 1H), 2.00–2.36 (m, 4H), 2.55 (m, 1H), 3.11 (m, 1H), 3.26 (m, 1H), 5.02 (br.s, 1H), 6.53 (m, 1H). MS (ESI) m/z 344.26 (M−H⁻).

5.30 Example 30

3-[(tert-Butoxycarbonyl)aminomethyl]-5-Methyl-Hexanoic Acid (37)

To a stirred suspension of pregabalin (950 mg, 4.85 mmol) and NaOH (452 mg, 11.32 mmol) in water (20 mL) was added a solution of di-tert-butyl dicarbonate (8.49 mmol) in dioxane (20 mL) at room temperature. The resulting mixture was stirred at room temperature for 30 min. The solvent was removed in vacuo, and the residue was washed with diethyl ether to remove the excess of di-tert-butyl dicarbonate, then was acidified to pH 3 with citric acid. The resulting mixture was extracted with ethyl acetate (3×50 mL) and the combined organic fractions were washed with brine and dried over anhydrous $Na_2SO_4$. Filtration and removal of the solvent in vacuo afforded the title compound (37) (1.24 g, 98%). $^1$H-NMR ($CD_3OD$, 400 MHz): δ 0.89 (2 d, 6H), 1.17 (m, 2H), 1.44 (s, 9H), 1.65 (m, 2H), 2.08 (m, 11H), 2.31 (m, 2H), 3.06 (m, 1H), 3.22 (m, 1H), 4.77 (br.s, 1H). MS (ESI) m/z 258.15 (M−H⁻).

5.31 Example 31

Benzyl 3-[(tert-Butoxycarbonyl)aminomethyl]-5-Methyl-Hexanoate (38)

To a stirred suspension of (37) (1.24 g, 4.78 mmol) and $Cs_2CO_3$ (1.56 g, 4.78 mmol) in DMF (20 mL) was added benzyl bromide (0.56 mL, 4.68 mmol). The resulting mixture was stirred at ambient temperature until the reaction was complete (~2 h, as monitored by LC/MS). The mixture was poured into ice water and extracted with dichloromethane. The combined organic phase was washed with water and brine, then dried over anhydrous $Na_2SO_4$. Filtration and removal of the solvent in vacuo afforded the title compound (38) (1.77 g, 100%), which was used without further purification in the following example. $^1$H-NMR ($CDCl_3$, 400 MHz): δ 0.86 (2 d, 6H), 1.13 (m, 2H), 1.42 (s, 9H), 1.62 (m, 1H), 2.31 (m, 2H), 3.00 (m, 1H), 3.18 (m, 1H), 4.75 (br.s, 1H), 5.10 (s, 2H), 7.33 (m, 5H). MS (ESI) m/z 372.30 (M+Na⁺).

5.32 Example 32

Benzyl 3-Aminomethyl-5-Methyl-Hexanoate Hydrochloride (39)

A solution of (38) (1.77 g, 4.78 mmol) in 4M HCl in dioxane (20 mL) was stirred at ambient temperature for 30 min. Removal of the solvent in vacuo afforded the title compound (39) as a white crystalline solid (1.4 g, 88%). $^1$H-NMR ($CDCl_3$, 400 MHz): δ 0.85 (d, 6H), 1.17 (m, 1H), 1.30 (m, 1H), 1.58 (m, 1H), 2.32 (m, 1H), 2.57 (m, 2H), 3.03 (m, 2H), 5.09 (s, 2H), 7.30 (m, 5H), 8.39 (br.s, 3H). MS (ESI) m/z 250.25 (M+H⁺).

5.33 Example 33

Benzyl 3-{[(α-Chloroethoxy)carbonyl]aminomethyl}-5-Methyl-Hexanoate (40)

To a stirred solution of (39) (428 mg, 1.51 mmol) in dichloromethane at 0° C. was added N-methylmorpholine (0.33 mL, 3.02 mmol) and 1-chloroethyl chloroformate (0.164 mL, 1.51 mmol). The resulting solution was stirred at 0° C. until the reaction was complete (~30 min, as monitored by TLC) and then was diluted with dichloromethane, washed successively with cold 1N HCl solution, water and brine, then dried over anhydrous $Na_2SO_4$. Filtration and removal of the solvent in vacuo afforded the title compound (40) as a mixture of two diastereomers (530 mg, 100%), which was used without further purification in the following example. $^1$H-NMR ($CDCl_3$, 400 MHz): δ 0.87 (m, 6H), 1.13 (m, 2H), 1.63 (m, 1H), 1.76 (m, 3H), 2.15 (m, 1H), 2.34 (m, 2H), 3.10 (m, 1H), 3.27 (m, 1H), 5.11 (br.s, 3H), 6.53 (q, 1H), 7.33 (m, 5H).

5.34 Example 34

Benzyl 3-{[(α-Isobutanoyloxyethoxy)carbonyl]aminomethyl}-5-Methyl-Hexanoate (41)

A solution of (40) (0.53 g, 1.50 mmol) in isobutyric acid (1 mL) was added to a mixture of isobutyric acid (0.96 mL, 10.8 mmol) and N-methylmorpholine (1.14 mL, 10.4 mmol) at room temperature. The resulting reaction mixture was stirred at room temperature for 48 h. The reaction mixture was diluted with dichloromethane, washed successively with water, 10% aqueous NaHCO$_3$ solution and brine, then dried over anhydrous Na$_2$SO$_4$. After filtration and removal of the solvent in vacuo, the residue was purified by flash chromatography on silica gel, eluting with 5% ethyl acetate in hexane to afford the title compound (41) as a mixture of two diastereomers (400 mg, 66%). $^1$H-NMR (CDCl$_3$, 400 MHz): δ 0.85 (m, 6H), 1.14 (m, 8H), 1.44 (m, 3H), 1.62 (m, 1H), 2.13 (m, 1H), 2.32 (m, 2H), 2.51 (m, 1H), 3.06 (m, 1H), 3.24 (m, 1H) 4.95 (m, 1H), 5.10 (s, 2H), 6.76 (q, 1H).

5.35 Example 35

3-{[(α-Isobutanoyloxyethoxy)carbonyl]aminomethyl}-5-Methyl-Hexanoic Acid (33)

A solution of (41) (270 mg, 0.663 mmol) in ethanol (20 mL) was stirred with 10% Pd on carbon (11 mg) in a 50 mL round-bottomed flask under an atmosphere of hydrogen gas (balloon). The reaction was judged complete in 30 min. (monitoring by TLC and LC/MS). The mixture was filtered through a pad of Celite, and the solvent removed in vacuo to afford the title compound (33) as a mixture of two diastereomers (177 mg, 84%). $^1$H-NMR (CDCl$_3$, 400 MHz): δ 0.89 (m, 6H), 1.16 (m, 8H), 1.46 (d, 3H), 1.66 (m, 1H), 2.11–2.36 (m, 3H), 2.52 (m, 1H), 3.11 (m, 1H), 3.27 (m, 1H), 5.08 (t, 1H), 6.77 (m, 11H). MS (ESI) m/z 316.20 (M–H$^-$).

5.36 Example 36

Benzyl 3-{[(α-Chloroisobutoxy)carbonyl]aminomethyl}-5-Methyl-Hexanoate (42)

To a stirred solution of (39) (594 mg, 2.38 mmol) in dichloromethane at 0° C. was added N-methylmorpholine (0.523 mL, 4.77 mmol) and 1-chloro-2-methylpropyl chloroformate (0.347 mL, 2.38 mmol). The resulting solution was stirred at 0° C. until the reaction was complete (~30 min, as monitored by TLC) and then was diluted with dichloromethane, washed successively with cold 1N HCl solution, water and brine, then dried over anhydrous Na$_2$SO$_4$. Filtration and removal of the solvent in vacuo afforded the title compound (42) as a mixture of two diastereomers (840 mg, 92%), which was used without further purification in the following example. $^1$H-NMR (CDCl$_3$, 400 MHz): δ 0.86 (2 d, 6H), 1.02 (2 d, 6H), 1.15 (m, 2H), 1.63 (m, 1H), 2.14 (m, 2H), 2.34 (m, 2H), 3.10 (m, 1H), 3.28 (m, 1H), 5.11 (br.s, 3H), 6.29 (d, 1H), 7.31 (m, 5H).

5.37 Example 37

Benzyl 3-{[(α-Isobutanoyloxyisobutoxy)carbonyl]-aminomethyl}-5-Methyl-Hexanoate (43)

A solution of (42) (840 mg, 2.19 mmol) in isobutyric acid (1 mL) was added to a mixture of isobutyric acid (1 mL, 10.95 mmol) and N-methylmorpholine (1.2 mL, 10.95 mmol) at room temperature. The resulting reaction mixture was stirred at room temperature for 48 h. The reaction mixture was diluted with dichloromethane (100 mL), washed successively with water, 10% aqueous NaHCO$_3$ solution and brine, then dried over anhydrous Na$_2$SO$_4$. After filtration and removal of the solvent in vacuo, the residue was purified by flash chromatography on silica gel, eluting with 5% ethyl acetate in hexane to afford the title compound (43) as a mixture of two diastereomers (430 mg, 45%). $^1$H-NMR (CDCl$_3$, 400 MHz): δ 0.85 (2 d, 6H), 0.94 (d, 6H), 1.16 (m. 8H), 1.62 (m, 1H), 2.00 (m, 1H), 2.12 (m, 1H), 2.32 (m., 2H), 2.54 (m, 1H), 3.08 (m, 1H), 3.24 (m, 1H), 4.94 (t, 1H), 5.10 (s, 2H), 6.55 (d, 1H), 7.33 (m, 5H).

5.38 Example 38

3-{[(α-Isobutanoyloxyisobutoxy)carbonyl]aminomethyl}-5-Methyl-Hexanoic Acid (36)

A solution of (43) (430 mg, 0.987 mmol) in ethanol (30 mL) was stirred with 10% Pd on carbon (50 mg) in a 100 mL round-bottomed flask under an atmosphere of hydrogen gas (balloon). The reaction was judged complete in 40 min. (monitoring by TLC and LC/MS). The mixture was filtered through a pad of Celite, and the solvent removed in vacuo to afford the title compound (36) as a mixture of two diastereomers (340 mg, 100%). $^1$H-NMR (CDCl$_3$, 400 MHz): 0.88 (m, 6H), 0.95 (d, 6H), 1.17 (m. 8H), 1.64 (m, 1H), 2.00–2.36 (m, 4H), 2.55 (m, 1H), 3.11 (m, 1H), 3.26 (m, 1H), 5.02 (br.s, 1H), 6.53 (m, 1H). MS (ESI): m/z 344.26 (M–H$^-$).

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated by reference in their entirety.

What is claimed is:

1. A method of synthesizing a compound of Formula (I) comprising:

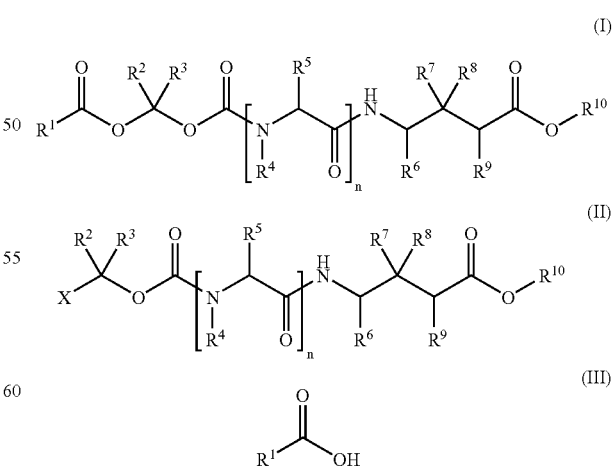

contacting a compound of Formula (II), a compound of Formula (III) and at least one equivalent of a metal salt or an organic base or a combination thereof wherein:

X is F, Cl, Br or I;

n is 0 or 1;

$R^1$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or optionally, $R^2$ and $R^3$ together with the atom to which they are bonded form a cycloalkyl, substituted cycloalkyl, cycloheteroalkyl or substituted cycloheteroalkyl ring;

$R^4$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^5$ is hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, or optionally, $R^4$ and $R^5$ together with the atoms to which they are attached form a cycloheteroalkyl or substituted cycloheteroalkyl ring;

$R^6$ and $R^9$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^7$ and $R^8$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, $R^7$ and $R^8$ together with the carbon atom to which they are attached form a cycloalkyl, substituted cycloalkyl, cycloheteroalkyl, substituted cycloheteroalkyl or bridged cycloalkyl ring; and $R^{10}$ hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl.

2. The method of claim 1, wherein the compound of Formula (I) is derived from a GABA analog of Formula (IV):

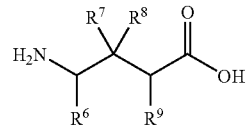

(IV)

in which the GABA analog of Formula (IV) is selected from the group consisting of:

1-Aminomethyl-1-cyclohexane acetic acid (i.e., gabapentin);
1-Aminomethyl-1-(3-methylcyclohexane) acetic acid;
1-Aminomethyl-1-(4-methylcyclohexane) acetic acid;
1-Aminomethyl-1-(4-isopropylcyclohexane) acetic acid;
1-Aminomethyl-1-(4-tert-butylcyclohexane) acetic acid;
1-Aminomethyl-1-(3,3-dimethylcyclohexane) acetic acid;
1-Aminomethyl-1-(3,3,5,5-tetramethylcyclohexane) acetic acid;
1-Aminomethyl-1-cyclopentane acetic acid;
1-Aminomethyl-1-(3-methylcyclopentane) acetic acid;
1-Aminomethyl-1-(3,4-dimethylcyclopentane) acetic acid;
7-Aminomethyl-bicyclo[2.2.1]hept-7-yl acetic acid;
9-Aminomethyl-bicyclo[3.3.1]non-9-yl acetic acid;
4-Aminomethyl-4-(tetrahydropyran-4-yl) acetic acid;
3-Aminomethyl-3-(tetrahydropyran-3-yl) acetic acid;
4-Aminomethyl-4-(tetrahydrothiopyran-4-yl) acetic acid;
3-Aminomethyl-3-(tetrahydrothiopyran-3-yl) acetic acid;
(S)-3-Aminomethyl-5-methyl-hexanoic acid (i.e. pregabalin);
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-phenyl-hexanoic acid;
3-Aminomethyl-5-phenyl-pentanoic acid;
3-Aminomethyl-4-cyclobutyl-butyric acid;
3-Aminomethyl-4-cyclopentyl-butyric acid;
3-Aminomethyl-4-cyclohexyl-butyric acid;
3-Aminomethyl-4-phenoxy-butyric acid;
3-Aminomethyl-5-phenoxy-hexanoic acid; and
3-Aminomethyl-5-benzylsulfanyl-pentanoic acid.

3. The method of claim 1 wherein the compound of Formula (I) is a compound of Formulae (V) or (VI):

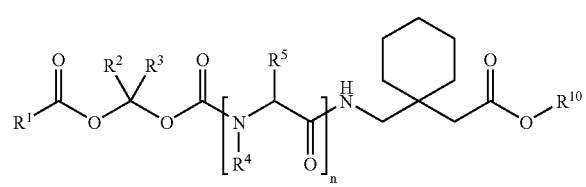

(V)

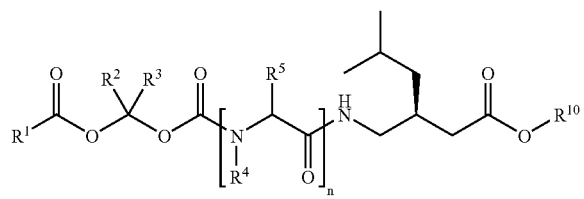

and n is 0.

4. The method of claim 3, wherein $R^1$ is methyl, ethyl, propyl, isopropyl, n-butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is hydrogen, methyl, ethyl, propyl, isopropyl, n-butyl, isobutyl, sec-butyl, tert-butyl, cyclohexyl or phenyl, and $R^3$ is hydrogen.

5. The method of claim 3, wherein $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is methyl and $R^3$ is methyl.

6. The method of claim 3, wherein $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl, $R^2$ is methoxycarbonyl, ethoxycarbonyl, isopropoxycarbonyl or cyclohexyloxycarbonyl and $R^3$ is methyl.

7. The method of claim 3, wherein, $R^1$ is methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, cyclobutyl, cyclopentyl, cyclohexyl, phenyl, 4-methoxyphenyl, benzyl, phenethyl, styryl or 3-pyridyl and $R^2$ and $R^3$ together with the atom to which they are attached form a cyclohexyl ring.

8. The method of claim 3, wherein $R^2$ is methyl, methoxycarbonyl, ethoxycarbonyl, isopropoxycarbonyl or cyclohexyloxycarbonyl and $R^3$ is methyl.

9. The method of claim 3, wherein $R^1$ is methyl, ethyl, n-propyl, isopropyl, n-butyl, isobutyl, sec-butyl, tert-butyl, 1,1-dimethoxyethyl, 1,1-diethoxyethyl, cyclobutyl, cyclopentyl or cyclohexyl and $R^{10}$ hydrogen, allyl, benzyl or trimethylsilyl.

10. The method of claim 3, wherein $R^2$ is hydrogen, methyl, ethyl, n-propyl, isopropyl, n-butyl, isobutyl, sec-butyl or tert-butyl and $R^3$ is hydrogen.

11. The method of claim 3, wherein $R^1$ is methyl, ethyl, n-propyl, isopropyl, n-butyl, isobutyl, sec-butyl, tert-butyl, 1,1-dimethoxyethyl, 1,1-diethoxyethyl, cyclobutyl, cyclopentyl or cyclohexyl, $R^{10}$ is hydrogen, allyl, benzyl or trimethylsilyl, $R^2$ is hydrogen, methyl, ethyl, isopropyl, n-butyl, isobutyl, sec-butyl or tert-butyl and $R^3$ is hydrogen.

12. The method of claim 3, wherein $R^1$ is ethyl or isopropyl, $R^{10}$ hydrogen, allyl, benzyl or trimethylsilyl, $R^2$ is methyl, n-propyl or isopropyl and $R^3$ is hydrogen.

13. The method of claim 3, wherein $R^1$ is isopropyl $R^{10}$ is benzyl $R^2$ is methyl and $R^3$ hydrogen.

14. The method of claim 3, wherein $R^1$ is ethyl or isopropyl, $R^{10}$ hydrogen, allyl, benzyl or trimethylsilyl, $R^2$ is methyl, n-propyl or isopropyl, $R^3$ is hydrogen and X is chloro.

15. The method of claim 3, wherein $R^1$ is isopropyl $R^{10}$ is benzyl $R^2$ is methyl, $R^3$ is hydrogen and X is chloro.

16. The method of claim 1, wherein the ratio of the compound of Formula (II) to the compound of Formula (III) is between about 1:1 and about 1:20.

17. The method of claim 1 further comprising contacting the compound of Formula (II) and the compound of Formula (III) and at least one equivalent of a metal salt or an organic base or a combination thereof with an organic solvent.

18. The method of claim 17, wherein the solvent is dichloromethane, dichloroethane, chloroform, toluene, dimethylformamide, dimethylacetamide, N-methylpyrrolidinone, dimethyl sulfoxide, pyridine, ethyl acetate, acetonitrile, acetone, 2-butanone, methyl tert-butyl ether, methanol, ethanol, isopropanol, tert-butanol, water, hexamethylphosphoramide or combinations thereof.

19. The method of claim 1, wherein the metal salt is a Ag, Hg, Na, K, Li, Cs, Ca, Mg or Zn salt.

20. The method of claim 1, wherein the organic base is triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, 1,5-diazabicyclo[4.3.0]undec-7-ene or combinations thereof.

21. The method of claim 1 wherein the compound of Formula (III) is a liquid.

22. The method of claim 21, wherein the compound of Formula (III) is acetic acid, methoxyacetic acid, ethoxyacetic acid, propionic acid, butyric acid, isobutyric acid, pivalic acid, valeric acid, isovaleric acid, 2-methylbutyric acid, cyclobutanecarboxylic acid, cyclopentanecarboxylic acid or cyclohexanecarboxylic acid.

23. The method of claim 22, wherein the compound of Formula (III) is isobutyric acid.

24. The method of claim 1, further comprising contacting the compound of Formula (II), the compound of Formula (III) and the metal salt or the organic base or a combination thereof at a temperature between about −25° C. and about 120° C.

25. The method of claim 24, wherein, the temperature is between about 0° C. and about 25° C.

26. The method of claim 1 further comprising contacting the compound of Formula (II), the compound of Formula (III) and the metal salt or the organic base or a combination thereof with a catalytic amount of an iodide salt.

27. The method of claim 26, wherein the iodide salt is sodium iodide, potassium iodide, tetramethylammonium iodide, tetraethylammonium iodide or tetrabutylammonium iodide.

* * * * *